(12) United States Patent
Suzuki et al.

(10) Patent No.: US 7,603,160 B2
(45) Date of Patent: Oct. 13, 2009

(54) INTRA-SUBJECT POSITION DISPLAY SYSTEM

(75) Inventors: Katsuya Suzuki, Sagamihara (JP); Katsuyoshi Sasagawa, Hino (JP); Takemitsu Honda, Hino (JP); Katsumi Hirakawa, Sagamihara (JP); Seiichiro Kimoto, Hachioji (JP); Ayako Nagase, Hachioji (JP); Kazutaka Nakatsuchi, Hino (JP)

(73) Assignee: Olympus Corporation, Tokyo (JP)

(*) Notice: Subject to any disclaimer, the term of this patent is extended or adjusted under 35 U.S.C. 154(b) by 602 days.

(21) Appl. No.: 11/101,264

(22) Filed: Apr. 7, 2005

(65) Prior Publication Data
US 2007/0002038 A1  Jan. 4, 2007

(30) Foreign Application Priority Data
Apr. 7, 2004  (JP)  ............................. 2004-113191

(51) Int. Cl.
*A61B 5/05* (2006.01)
*A61B 5/00* (2006.01)
*A61B 19/00* (2006.01)

(52) U.S. Cl. ..................... 600/424; 128/899; 600/302; 600/476; 600/160

(58) Field of Classification Search ............... 600/476, 600/109, 424; 128/903, 899
See application file for complete search history.

(56) References Cited

U.S. PATENT DOCUMENTS

| | | | |
|---|---|---|---|
| 5,604,531 A * | 2/1997 | Iddan et al. | 348/76 |
| 6,233,476 B1 * | 5/2001 | Strommer et al. | 600/424 |
| 6,456,668 B1 * | 9/2002 | MacLellan et al. | 375/283 |
| 7,144,366 B2 * | 12/2006 | Takizawa et al. | 600/117 |
| 7,214,182 B2 * | 5/2007 | Shimizu et al. | 600/117 |
| 2002/0173718 A1 * | 11/2002 | Frisch et al. | 600/424 |
| 2002/0198439 A1 * | 12/2002 | Mizuno | 600/109 |
| 2003/0023150 A1 * | 1/2003 | Yokoi et al. | 600/300 |
| 2003/0229268 A1 * | 12/2003 | Uchiyama et al. | 600/109 |
| 2004/0111011 A1 * | 6/2004 | Uchiyama et al. | 600/160 |
| 2004/0181127 A1 * | 9/2004 | Matsumoto et al. | 600/101 |
| 2004/0204630 A1 * | 10/2004 | Gilad | 600/160 |
| 2004/0225184 A1 * | 11/2004 | Shimizu et al. | 600/112 |
| 2005/0043634 A1 * | 2/2005 | Yokoi et al. | 600/476 |
| 2005/0065407 A1 * | 3/2005 | Nakamura et al. | 600/160 |
| 2005/0143642 A1 * | 6/2005 | Minai et al. | 600/407 |

(Continued)

FOREIGN PATENT DOCUMENTS

JP  2003-19111  1/2003

*Primary Examiner*—Eric F Winakur
*Assistant Examiner*—Helene Bor
(74) *Attorney, Agent, or Firm*—Scully, Scott, Murphy & Presser, P.C.

(57) ABSTRACT

An intra-subject position display system for displaying a position of an intra-subject device, which is introduced into a subject and moves therein, wherein a relative position of the intra-subject device to an outer surface of the subject is detected and displayed. The position of the intra-subject device is displayed in a relation with the outer surface of the subject. Thereby, it is possible to easily determine in which site of the subject the intra-subject device exists. The present invention is effective to recognize a position of, for example, a capsule type endoscope or a test capsule therefor in the subject (e.g., a human body). To recognize the outer surface of the subject, for example, a plurality of radio devices are arranged on the outer surface of the subject and their radio signals are analyzed.

12 Claims, 14 Drawing Sheets

U.S. PATENT DOCUMENTS

| | | | |
|---|---|---|---|
| 2005/0143649 A1* | 6/2005 | Minai et al. | 600/410 |
| 2006/0169293 A1* | 8/2006 | Yokoi et al. | 128/899 |
| 2006/0183993 A1* | 8/2006 | Horn | 600/407 |
| 2006/0224063 A1* | 10/2006 | Segawa et al. | 600/424 |
| 2006/0243288 A1* | 11/2006 | Kim et al. | 128/899 |
| 2006/0264709 A1* | 11/2006 | Fujimori et al. | 600/130 |
| 2007/0055099 A1* | 3/2007 | Kimoto | 600/109 |
| 2007/0135680 A1* | 6/2007 | Mizuno | 600/118 |
| 2007/0135684 A1* | 6/2007 | Suzushima et al. | 600/160 |
| 2007/0197869 A1* | 8/2007 | Uchiyama et al. | 600/114 |

* cited by examiner

INTRA-SUBJECT POSITION DISPLAY SYSTEM

CROSS-REFERENCE TO RELATED APPLICATION

This application is based upon and claims the benefit of priority from prior Japanese Patent Application No. 2004-113191, filed Apr. 7, 2004, the entire contents of which is incorporated herein by reference.

BACKGROUND OF THE INVENTION

1. Field of the Invention

The present invention relates to an intra-subject position display system for displaying a position of an intra-subject device, which is introduced into a subject and moves inside the subject.

2. Description of the Related Art

Recently, in the field of endoscopy, there has been suggested a swalloable capsule type endoscope. The capsule type endoscope is provided with an imaging function and a radio communication function. The capsule type endoscope has a function of moving inside the body cavity (for example, inside a stomach, small intestine, or other organs) by the organ's peristaltic motion and taking images sequentially after being swallowed from the mouth of the subject for observation (examination) until it is excreted naturally.

While it moves inside the body cavity, image data picked up in the subject by the capsule type endoscope is sequentially transmitted to the outside by radio communication and then stored in an external memory. The subject such as a patient can act freely after swallowing the capsule type endoscope until it is excreted, by carrying a receiver having the radio communication and memory functions. After the capsule type endoscope is excreted, a doctor or a nurse can output images of the organ to a display on the basis of the image data stored in the memory for a diagnosis.

In this type of capsule type endoscope, there has been suggested a system comprising a receiver with a function of detecting a position of a capsule type endoscope in the subject, for example, in order to pick up endoscopic images of a specific organ inside the subject. As an example of the capsule endoscopic system having this type of position detecting function, there has already been known one in which a radio communication function built in the capsule type endoscope is also used for a positional detection.

For example, in a capsule endoscopic system disclosed in Japanese Laid-Open Patent Publication (Kokai) No. 2003-19111, a receiver provided outside the subject has a plurality of antenna elements and receives a radio signal transmitted from a capsule type endoscope with the individual antenna elements. The foregoing capsule endoscopic system detects a position of the capsule type endoscope in the subject on the basis of differences of reception intensity in the individual antenna elements.

In the conventional capsule endoscopic system, however, it is hard for a doctor, a nurse, or the like to understand the picked-up image's position in the subject. This problem will be described hereinafter.

In the conventional capsule endoscopic system, the position of the capsule type endoscope is detected on the basis of differences of reception intensity in the plurality of antenna elements provided in the receiver in response to the radio signal transmitted from the capsule type endoscope. When this arrangement is adopted, however, it is possible to detect the position of the capsule type endoscope in relation to the receiver, but it is hard to detect a relative position of the capsule type endoscope in the subject.

A subject has individual variations depending on the build of the subject's body, for example, according to sex, age, race or the like. If only the position of the capsule type endoscope relative to the receiver (so to speak, an absolute position) is derived, it is hard for a doctor or nurse to realize where the capsule type endoscope locates within the subject based on the absolute position. Therefore, it is hard to determine in which organ of the subject the capsule type endoscope positions at a given time. In other words, a position detecting mechanism in the conventional capsule endoscopic system is only capable of teaching an absolute position such as the position of the capsule type endoscope in relation to the receiver. In some cases, such a system does not fully contribute to improve a convenience on a diagnosis or the like.

This invention aims to provide an intra-subject position display system enabling an operator such as a doctor to easily recognize a relative position relationship between a subject and an intra-subject device such as a capsule type endoscope introduced into the subject.

BRIEF SUMMARY OF THE INVENTION

According to one aspect of the present invention, there is provided an intra-subject position display system for displaying a position of an intra-subject device, which is introduced into a subject and moves therein, wherein a relative position of the intra-subject device to an outer surface of the subject is detected and displayed.

Thereby, an operator can see the position of the intra-subject device in a relation with the outer surface of the subject, by which the operator can easily understand the position of the intra-subject device in the subject.

For example, a display device for displaying the foregoing relative position displays an outer surface image of the subject and an image of the intra-subject device. The image of the intra-subject device is disposed on an area corresponding to the relative position of the intra-subject device to the outer surface image.

Thereby, the outer surface image and the image of the intra-subject device are displayed and therefore the positional relations between them can be easily understood.

For example, there is the following feature for detecting the relative position of the intra-subject device to the outer surface of the subject. Outer surface information can be derived by using a plurality of outer surface sensors disposed on the outer surface of the subject and an outer surface information deriving section for deriving the outer surface information of the subject on the basis of positions of the outer surface sensors. An absolute position of the intra-subject device can be detected by using a magnetic field sensor for detecting the intensity of a magnetic field generated by a magnetic field generating section within the intra-subject device.

In addition to the example, there are provided a positional relation deriving section and a relative position deriving section. The positional information deriving section derives a positional relation between the outer surface of the subject and the magnetic field sensor. The relative position information deriving section derives a relative position information of the outer surface of the subject and the intra-subject device based on the positional information derived by the positional information deriving section and the magnetic field intensity detected by the magnetic field sensor.

In this example, the magnetic field sensor can be disposed in a fixed positional relation with at least one of the outer surface sensors. The positional relation deriving section derives the positional relation between the outer surface of the subject and the magnetic field sensor on the basis of the position of the outer surface sensor disposed in the fixed positional relation with the magnetic field sensor. Thereby, due to the fixed relative position of the magnetic field sensor and the outer surface sensor, calculations for deriving the positional relationship become easy.

It is possible that the outer surface sensors detect the position of the outer surface by using a radio signal. For example, a first radio section is disposed in a reference position and the plurality of outer surface sensors are provided with a second radio section for a transmission of a radio signal to or from the first radio section. A distance between the reference position and the outer surface sensor is derived on the basis of a reception intensity of at least one of the first radio section and the second radio section in the transmission of the radio signal between the first radio section and the second radio section (a distance deriving section). Then, the position of the outer surface sensor is derived on the basis of the distances derived by the distance deriving section (an outer surface sensor position deriving section). Furthermore, outer surface information of the subject is derived on the basis of the position derived by the outer surface sensor position deriving section (an outer surface information deriving section).

In this example, preferably there is a mechanism for identifying each of the outer surface sensors. For example, the plurality of second radio sections transmit radio signals having different frequencies from one another and the outer surface information deriving section identifies a transmission source of a received radio signal by analyzing a frequency of the radio signal received by the first radio section (spectrum analysis section). Alternatively, the plurality of second radio sections include respective RFID tags storing different identification information from one another and the outer surface information deriving section identifies a transmission source of the received radio signal on the basis of the identification information included in the radio signal received by the first radio section (a transmission source identifying section).

Moreover, the intra-subject position display system can be provided with a position information database. For example, the outer surface information deriving section further includes a position information database storing correspondences information between respective distances between the plurality of outer surface sensors and the reference position and the positions of the outer surface sensors, and the outer surface sensor position deriving section derives positions corresponding to the distances derived by the distance deriving section from the information stored in the position information database.

Various improvements are applicable to the first radio section provided in the reference position. For example, a plurality of first radio sections can be provided. The outer surface sensor position deriving section can derive distances between a plurality of reference positions corresponding to the respective first radio sections and the outer surface sensors and can derive the positions of the outer surface sensors on the basis of the derived distances.

The outer surface sensor position deriving section can further include an oriented direction adjusting section for adjusting an oriented direction of the radio signal transmission of the first radio section, and an oriented direction determining section for determining a direction that cause the highest reception intensity in the transmission of the radio signal to or from the second radio section. The positions of the outer surface sensors are derived on the basis of the distances derived by the distance deriving section and the oriented direction determined by the oriented direction determining section.

The intra-subject device further can include an intra-subject information acquiring section for acquiring intra-subject information and a radio transmitting section for wirelessly transmitting the intra-subject information acquired by the intra-subject information acquiring section. In this example, the intra-subject position display system of this invention may further include a radio receiving section for receiving a radio signal including the intra-subject information transmitted from the radio transmitting section and the display device further displays a content of the radio signal received by the radio receiving section.

Furthermore, the intra-subject information acquiring section can include a lighting section for irradiating the inside of the subject and an imaging unit for acquiring images of the inside of the subject irradiated by the lighting section and the radio transmitting section can transmit a radio signal including image information acquired by taking the images using the imaging unit.

At least part of the plurality of sensors being provided on the outer surface of the subject and for detecting this position of the intra-subject device can accommodate a radio signal generation unit for detecting the outer surface of the subject. In this example, some of the sensors for detecting the position of the intra-subject device are also used for detecting the outer surface of the subject. The intra-subject position display system may receive the radio signal generated by the radio signal generation unit and calculate the outer surface of the subject.

The intra-subject position display system can have at least of two types of a plurality of sensors, ones are for detecting the position of the intra-subject device introduced within the subject, and others provided on the outer surface of the subject for detecting position of the outer surface. However these sensors are not necessarily categorized into the at least two types, some of the sensors may have both functions. An intra-subject position display for displaying the positional relations between the outer surface of the subject and the intra-subject device based on the detection results of these types of sensors.

The intra-subject position display system can comprise a display device for displaying a relative position of the intra-subject device in the subject in relation to the outer surface of the subject having individual variations. Therefore, an observer such as a doctor or nurse can realize a relative position with the outer surface of the subject having individual variations, instead of an absolute position of the intra-subject device. For example, if the present invention is applied to a capsule type endoscope, it is possible to easily estimate which organ the capsule type endoscope is passing through.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENTS

Figure 1:
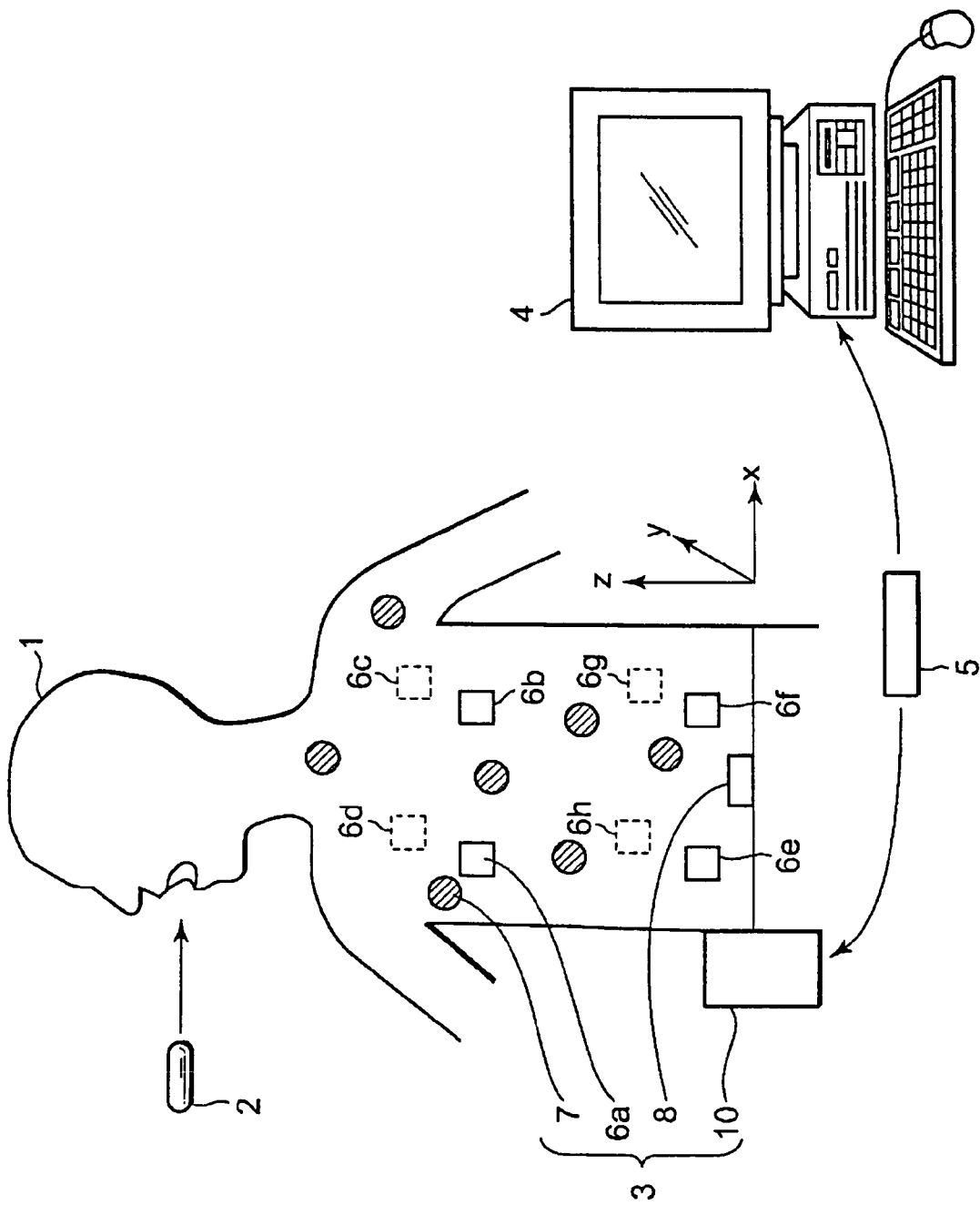
FIG. 1 is a schematic view showing an intra-subject position display system according to a first embodiment.

Preferred embodiments of the invention are described below with reference to the accompanying drawings.

An intra-subject position display system according to a first embodiment will now be described hereinafter. The intra-subject position display system according to the first embodiment includes a position detector 3, a display device 4, and a portable recording medium 5. The position detector 3 derives outer surface information on a shape or the like of an outer surface of a subject 1 and detects a relative position of a test capsule 2 (an example of an intra-subject device) to the outer surface. The display device 4 displays the relative position detected by the position detector 3. The portable recording medium 5 transmits information between the position detector 3 and the display device 4.

The test capsule 2 is a target of measurement with the intra-subject position display system and functions as an intra-subject device. The test capsule 2 is for use in conducting a preliminary examination to check whether there is a narrow area or the like where a capsule type endoscope is hard to pass through in the subject 1 before introducing the capsule type endoscope or the like into the subject 1. The intra-subject position display system according to the first embodiment has a function of clearly displaying a position of the test capsule 2 in the subject in a relation with the subject 1. By this function, an observer can easily understand where the test capsule 2 is located in the inside of the subject 1, independently of individual variations of the subject 1: For example, which organ the test capsule 2 is passing through at a given time.

Figure 2:
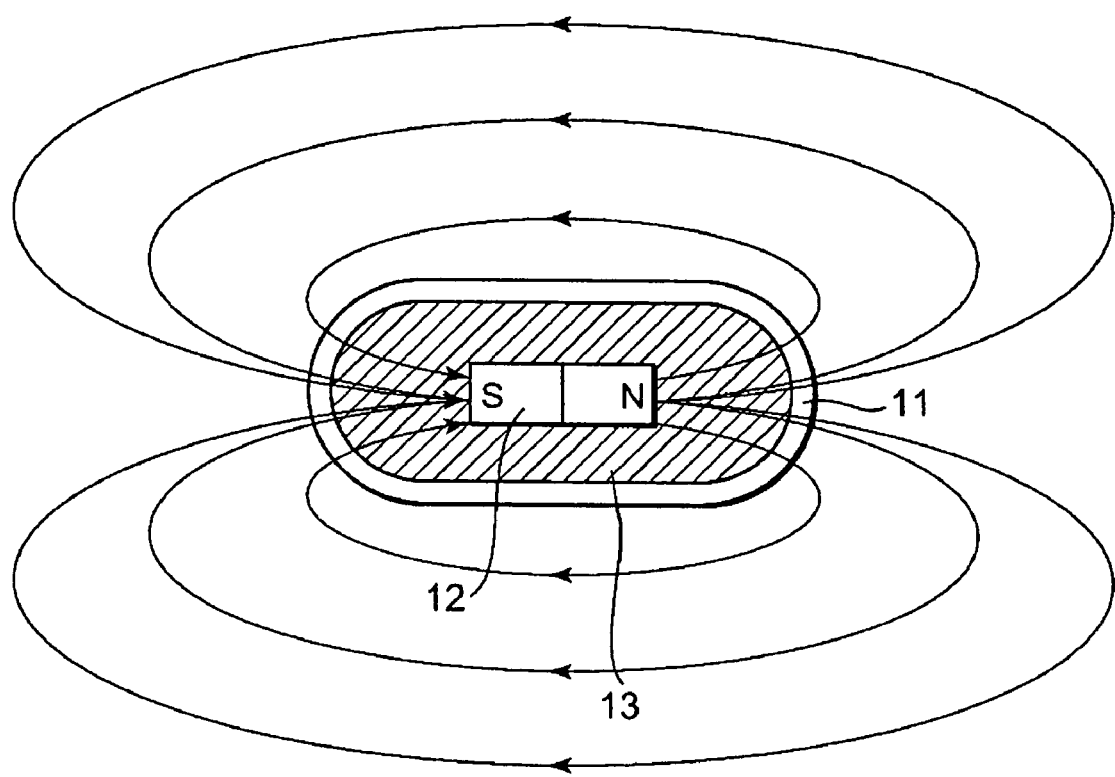
FIG. 2 is a block diagram showing a structure of a test capsule provided in the intra-subject position display system.

FIG. 2 is a schematic view showing a structure of the test capsule 2. As shown in FIG. 2, the test capsule 2 has a container 11 having the shape of a capsule similar to a container of a capsule type endoscope, a permanent magnet 12 disposed inside the container 11, and a filling member 13 for filling a gap between an inner surface of the container 11 and the permanent magnet 12. The container 11 is formed of, for example, a biocompatible material. Therefore, even if the test capsule 2 remains for several days within the subject 1, it does not adversely affect the subject 1 that is a living body.

The permanent magnet 12 (an example of a magnetic field generating section) is a permanent magnet of such size as to be contained in the container 11 and generates a static magnetic field with negligible time variance of a magnetic field intensity. Instead of the permanent magnet 12, for example, a coil or the like forming a static magnetic field with a supply of constant current can be used as a magnetic field generating section. The use of the permanent magnet 12, however, has an advantage of no need for a driving power.

The static magnetic field generated by the permanent magnet 12 can be represented by lines of magnetic force each having a shape of a closed curve, which are output from the north pole (N) and enter into the south pole (S) after traveling in the outside of the permanent magnet 12, as shown in FIG. 2. In this regard, while the traveling direction of the line of magnetic force has a locality dependency, an intensity of the static magnetic field represented by the line of magnetic force can be considered to be determined only according to a distance from the test capsule 2. In other words, the permanent magnet 12 built in the test capsule 2 is minute in size so as to be negligible in comparison with a distance between the test capsule 2 and each of magnetic field detectors 6a to 6h. In this condition, a magnetic field intensity P at a point that is a distance r apart from the test capsule 2 is expressed using a coefficient of proportionality α as follows:

$$P = \alpha/r^3 \quad (1)$$

The intra-subject position display system according to the first embodiment detects a position of the test capsule 2 on the basis of a relation expressed by the equation (1).

The filling member 13 fills the gap between the inner surface of the container 11 and the permanent magnet 12 to fix the position of the permanent magnet 12. A material not adversely affecting the subject 1 (for example, barium sulfate) is adopted to form the filling member 13. Since the barium sulfate can be used as a contrast agent for an x-ray examination, a position can be detected by an x-ray examination in addition to detecting a position by means of a magnetic force described later. Therefore, by comparing results of the detection of the test capsule 2 by the position detector with the detection of the test capsule 2 by the x-ray examination, the position of the test capsule 2 can be detected more accurately. Note that, however, the use of barium sulfate for the filling member 13 is not necessary, other arbitrary materials can be used as a filling member which need not be useful as a contrast agent.

The display device 4 is for use in displaying relative position information of the test capsule 2 acquired by the position detector 3 and displays an image based on data obtained from the portable recording medium 5. Specifically, the display device 4 can directly display the image by means of a CRT display, a liquid crystal display, or the like or can be output the image to some other medium like a printer.

The portable recording medium 5 is attachable or detachable to or from the position detector 3 and the display device 4 and is structured so as to be capable of outputting and recording information while being attached. Specifically, the portable recording medium 5 records information on the position of the test capsule 2 when inserted into a relative position information deriving device 10 included in the foregoing position detector 3 while the test capsule 2 is moving within a body cavity of the subject 1. Then, after the test capsule 2 is excreted from the subject 1, the portable recording medium 5 is removed from the relative position information deriving device 10 and inserted into'the display device 4 and then the display device 4 reads out the recorded data. The portable recording medium 5 exchanges data between the relative position information deriving device 10 and the display device 4, so that the subject 1 can act more freely while the test capsule 2 is moving inside the subject 1. Therefore, the subject 1 is not confined while the test capsule 2 traverses through the subject 1, but can move about freely. It is also possible, however, to directly wire the relative position information deriving device 10 with the display device 4 without the portable recording medium 5.

Subsequently, the position detector 3 is described below. As shown in FIG. 1, the position detector 3 includes magnetic field intensity detectors 6a to 6h, an outer surface sensor 7, an outer surface information deriving device 8, and a relative position information deriving device 10. The magnetic field intensity detectors 6a to 6h detect intensities of a static magnetic field generated by the test capsule 2. The outer surface sensor 7 is used for deriving outer surface information described later. The outer surface information deriving device 8 derives outer surface information of the subject 1 by detecting the position of the outer surface sensor 7. The relative position information deriving device 10 derives a relative position of the test capsule 2 to the outer surface of the subject 1 on the basis of the magnetic field intensities detected by the magnetic field detectors 6a to 6h and the outer surface information derived by the outer surface information deriving device 8.

Figure 3:
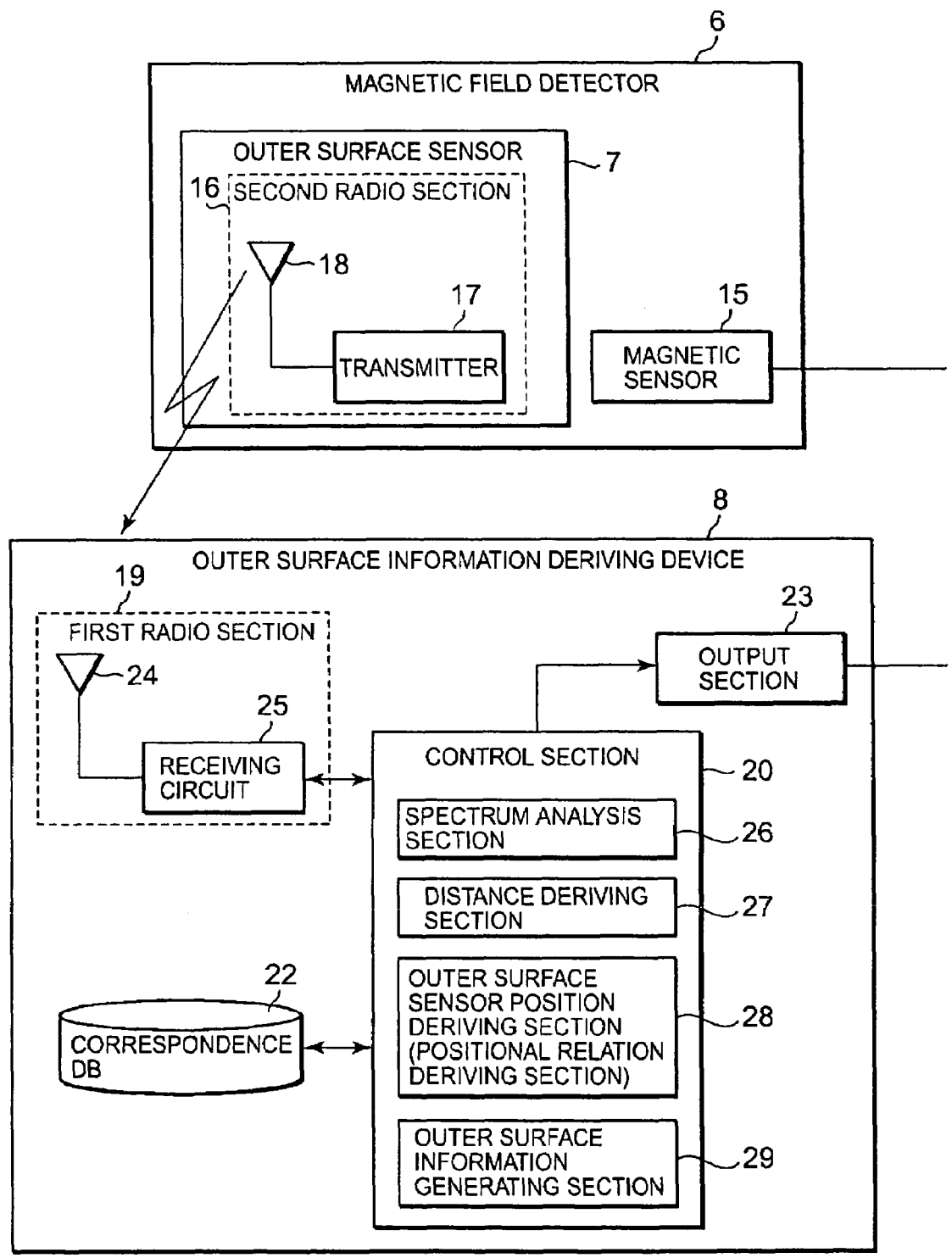
FIG. 3 is a block diagram showing a configuration of a magnetic field detector and of an outer surface information deriving device.

As shown in FIG. 1, the magnetic field detectors 6a to 6h are arranged on the outer surface of the subject 1 and detect intensities of the static magnetic field generated by the permanent magnet 12 included in the test capsule 2. FIG. 3 is a schematic illustration showing a specific configuration of the magnetic field detectors 6a to 6h (referred to generally or collectively by reference numeral 6) and that of the outer surface information deriving device 8. The magnetic field detector 6 includes a magnetic field sensor 15 for detecting a magnetic field and contains an outer surface sensor 7 for deriving a relative position of itself to the subject 1. The outer surface sensor 7 provided in the magnetic field detector 6 and the outer surface sensor 7 disposed outside the magnetic field detector 6 have the same configuration and functions. Hereinafter, these outer surface sensors 7 will be described collectively with reference to FIG. 3.

The outer surface sensor 7 is for use in deriving outer surface information in combination with the outer surface information deriving device 8. In other words, the outer surface information deriving device 8 has a function of deriving a position of the outer surface sensor 7 and a function of deriving outer surface information including information on a shape of the outer surface of the subject 1 on the basis of the derived position information of the plurality of outer surface sensors 7 within each magnetic field detector 6.

In the first embodiment, the outer surface sensor 7 has a function of transmitting a radio signal having a given intensity to the outer surface information deriving device 8 in order to enable the outer surface information deriving device 8 to detect the position of the outer surface sensor 7. Specifically, the outer surface sensor 7 includes a second radio section 16 for transmitting a radio signal of a given intensity to a first radio section 19 (described later) included in the outer surface information deriving device 8. The second radio section 16 includes a transmitter 17 for generating and outputting is a given radio signal and a transmitting antenna 18 for transmitting the radio signal output from the transmitter 17. A frequency of the radio signal output from the second radio section 16 is set so as to have a different value for each outer surface sensor 7. The reason for this is to determine which outer surface sensor 7 has transmitted a radio signal and what degree of reception intensity of the radio signal is according to a difference in frequency when the first radio section 19 receives the radio signal transmitted from each of the outer surface sensors 7.

The magnetic field sensor 15 of the magnetic field detector 6 is for use in detecting an intensity of a magnetic field caused by the test capsule 2 in a place where the magnetic field detector 6 of the position detector 3 is disposed. Specifically, the magnetic field sensor 15 is formed by using, for example, a magneto impedance (MI) sensor. The MI sensor has a feature in which, for example, an FeCoSiB amorphous wire is used as a magnetic sensitive medium. When a high-frequency current is supplied to the magnetic sensitive medium, the MI sensor detects a magnetic field intensity by using an MI effect that a magnetic impedance of the magnetic sensitive medium varies significantly due to an external magnetic field. While it is possible to use a magnetic field sensor 15 having other features, the MI sensor has an advantage that the magnetic field intensity can be detected at an especially high sensitivity. The information on the magnetic field intensity detected by the magnetic field sensor 15 is output to the relative position information deriving device 10 through wire cables and is used for deriving the position of the test capsule 2 relative to the magnetic field detector 6.

Subsequently, the outer surface information deriving device 8 will be described below. The outer surface information deriving device 8 is for use in deriving outer surface information of the subject 1 and outputting the derived outer surface information to the relative position information deriving device 10. Specifically, the outer surface information deriving device 8 includes a first radio section 19, a control section 20, a correspondence database 22, and an output section 23. The first radio section 19 receives a radio signal transmitted from the second radio section 16 included in the outer surface sensor 7. The control section 20 derives outer surface information. The correspondence database 22 is used when the control section 20 derives a position of the outer surface sensor 7. The output section 23 outputs the outer surface information derived by the control section 20 to the relative position information deriving device 10 through wire cables.

The first radio section 19 receives a radio signal transmitted from the second radio section 16 included in each of the outer surface sensors 7 and outputs the received radio signal to the control section 20 after performing demodulating or otherwise processing the received radio signal. Specifically, the first radio section 19 has a receiving antenna 24 and a receiving circuit 25 and at least the receiving antenna 24 is disposed at a given reference point.

The control section 20 has a function of deriving a distance between the outer surface information deriving device 8 (more properly, the receiving antenna 24) and the outer surface sensor 7 (more properly, the transmitting antenna 18) on the basis of the intensity of the radio signal received by the first radio section 19 and deriving outer surface information by using a result of the derivation. Specifically, the control section 20 includes a spectrum analysis section 26, a distance deriving section 27, an outer surface sensor position deriving section 28, and an outer surface information generating section 29. The spectrum analysis section 26 analyzes a frequency of the received radio signal and detects an intensity in each frequency component. The distance deriving section 27 derives a distance from the outer surface sensor 7 on the basis of the reception intensity detected by the spectrum analysis section 26. The outer surface sensor position deriving section 28 derives a position of the outer surface sensor 7 on the basis of information on the distance derived by the distance deriving section 27 and information stored in the correspondence database 22. The outer surface information generating section 29 derives outer surface information of the subject 1 on the basis of the position of the outer surface sensor 7 disposed on the outer surface of the subject 1. In this regard, the term "outer surface information" means information including data necessary to image at least a shape of the outer surface of the subject 1. In the first embodiment, it means information further including position information of the magnetic field detectors 6a to 6h relative to the outer surface of the subject 1.

In the first embodiment, a portion of a plurality of outer surface sensors 7 are built in some or all of the magnetic field detectors 6 and arranged in a fixed positional relation with the magnetic sensor 15. Therefore, the outer surface sensor position deriving section 28 derives the positions of the outer surface sensors 7, thereby deriving the position of the magnetic field sensor 15. Furthermore, the shape or the like of the outer surface of the subject 1 is derived on the basis of the positions of the outer surface sensors 7. Therefore, the derivation of the positions of the outer surface sensors 7 fixed in the positional relation with the magnetic field sensor 15 leads to a derivation of the positional relation of the magnetic field sensor 15 to the outer surface of the subject 1. In this sense, the outer surface sensor position deriving section 28 in the first embodiment serves as a positional relation deriving section for deriving a positional relation between the outer surface of the subject 1 and the magnetic field sensor 15. In other words, in the first embodiment, the shape or the like of the outer surface of the subject 1 is derived by deriving all positions of the outer surface sensors 7, thereby concurrently deriving the positions of the corresponding magnetic field detectors 6a to 6h to the outer surface. This generates outer surface information including the shape of the outer surface of the subject 1 and information regarding the positions of the magnetic field detectors 6a to 6h relative to the outer surface.

The correspondence database 22 has a function of storing correspondences information between the distances of the plurality of outer surface sensors 7 from the outer surface information deriving device 8 and specific positions of the outer surface sensors 7. A content of the correspondence stored in the correspondence database 22 can be arbitrary as long as it describes a correspondence between a distance and a position.

In the first embodiment, focusing on a relation between a positional variation and a distance of each of the outer surface sensors 7 involved in a change in a posture of the subject 1, the correspondence database 22 stores correspondence information between distances of all the outer surface sensors 7 from the reference point and their positions, instead of correspondences between distances of one of the plurality of outer surface sensors 7 from the first radio section 19 (reference point) and its position.

Figure 4:
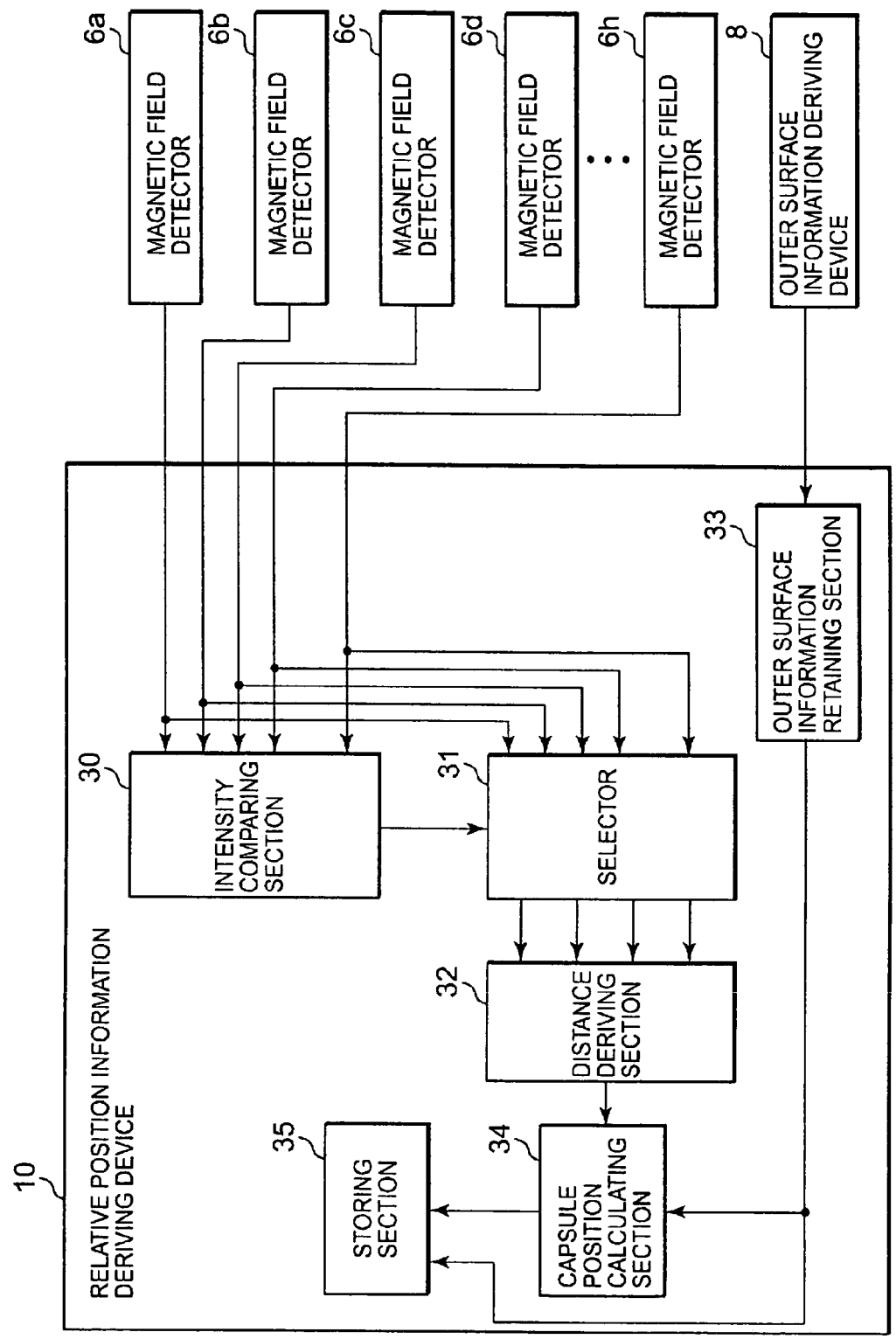
FIG. 4 is a block diagram showing a configuration of a relative position information deriving device included in the intra-subject position display system.

The following describes the relative position information deriving device 10. Referring to FIG. 4, there is shown a block diagram of a configuration of the relative position information deriving device 10. The relative position information deriving device 10 includes an intensity comparing section 30, a selector 31, a distance deriving section 32, an outer surface information retaining section 33, a capsule position calculating section 34, and a storing section 35. The intensity comparing section 30 compares intensities of the magnetic field detected by the magnetic sensors 15 included in the magnetic field detectors 6a to 6h, respectively. The selector 31 selects and outputs a portion of detection results from the magnetic field detectors 6a to 6h on the basis of a comparison result derived by the intensity comparing section 30. The distance calculating section 32 derives a distance between the test capsule 2 and the selected magnetic field detector 6 on the basis of the magnetic field intensities selected by the selector 31. The outer surface information retaining section 33 retains outer surface information output from the outer surface information deriving device 8. The capsule position calculating section derives a position of the test capsule 2 by means of given calculation processing on the basis of the distances of the magnetic field detectors 6a to 6h from the test capsule 2 derived by the distance deriving section 32 and the outer surface information retained in the outer surface information retaining section 33. The storing section 35 stores the calculation result of the capsule position calculating section 34 and the outer surface information from the outer surface information retaining section 33.

The selector 31 is for use in selecting a portion of the large number of magnetic field detectors 6a to 6h therefrom and in outputting intensities of the magnetic field detected by the selected magnetic field detectors 6 to the distance deriving section 32. While the selector 31 can use an arbitrary selection algorithm, it selects three magnetic field detectors 6 in descending order of intensity of the detected magnetic field on the basis of the comparison result of the intensity comparing section 30 and outputs intensities of the magnetic field detected by the magnetic field detectors 6. With this selection, the position of the test capsule 2 can be detected three-dimensionally and precisely by using data of the detected magnetic field having high intensities.

The distance deriving section 32 is for use in deriving distances between the magnetic field detectors 6 selected by the selector 31 and the test capsule 2 on the basis of the magnetic field intensities input via the selector 31. Specifically, the distance deriving section 32 derives the distances between the magnetic field detectors 6 and the test capsule 2 by performing calculation processing expressed by the equation (1) on the basis of the input magnetic field intensities.

The capsule position calculating section 34 is for use in deriving the position of the test capsule 2 to the outer surface of the subject 1 by performing given calculation processing using the distances derived by the distance deriving section 32 and the position information of the magnetic field detectors 6a to 6h retained in the outer surface information retaining section 33. The capsule position calculating section 34 has a function of deriving the position of the test capsule 2 to the outer surface of the subject 1 and then outputting a result of the derivation to the storing section 35.

The storing section 35 is for use in storing the derived position of the test capsule 2. Specifically, the storing section 35 has a function of outputting information input from the capsule position calculating section 34 to the portable recording medium 5.

The following describes an operation of the intra-subject position display system according to the first embodiment. The intra-subject position display system according to the first embodiment derives outer surface information including position information of the magnetic field detectors 6a to 6h by means of the outer surface information deriving device 8 and derives the position of the test capsule 2 to the outer surface of the subject 1 on the basis of detected positions of the magnetic field detectors 6a to 6h and magnetic field intensities detected by the magnetic field detectors 6a to 6h. Hereinafter, a description is made for the derivation of the outer surface information by the outer surface information deriving device 8, first, and then for the derivation of the relative position of the test capsule 2 by the relative position information deriving device 10.

Figure 5:
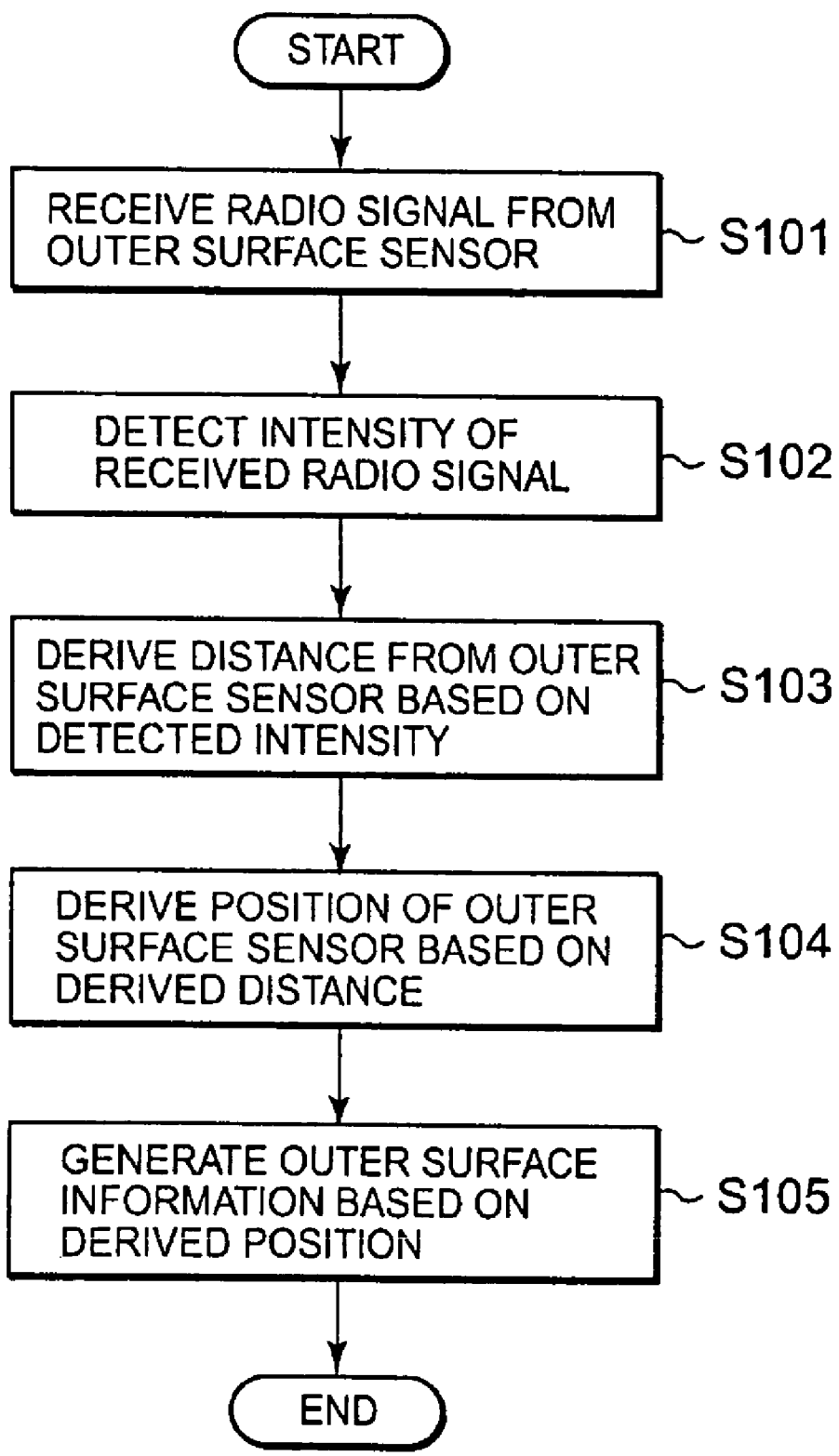
FIG. 5 is a flowchart for explaining an operation of deriving outer surface information.

Referring to FIG. 5, there is shown a flowchart for explaining an operation of deriving the positions of the magnetic field detectors 6a to 6h performed by the outer surface information deriving device 8. As shown in FIG. 5, the outer surface information deriving device 8 receives a radio signal transmitted from the second radio section 16 included in each of the outer surface sensors 7 by means of the first radio section 19 (step S101). It then detects an intensity of the radio signal transmitted from each of the outer surface sensors 7 by analyzing its frequency (step S102) and derives a distance between the outer surface sensor 7 and a reference point (for example, the first radio section 19) on the basis of the detected intensity by means of the distance deriving section 27 (step S103).

Thereafter, the outer surface information deriving device 8 derives positions of all the outer surface sensors 7 to the reference point by referencing the information stored in the correspondence database 22 on the basis of the derived distances (step S104). Finally, it calculates a shape or the like of the outer surface of the subject 1 on the basis of the derived positions of the outer surface sensors 7 and generates outer surface information by means of the outer surface information generating section 29 (step S105).

The derivation of the distances in step S103 will be briefly described below. The second radio section 16 provided in each of the outer surface sensors 7, which are included in the magnetic field detectors 6a to 6h or independently existing, has a function of radially transmitting a radio signal. An intensity of the radio signal transmitted from the second radio section 16 is in proportion to the minus cube of a traveling distance. By using this relation, the distance deriving section 27 derives a distance between the reference point and a magnetic field detector or an independently existing outer surface sensor 7 on the basis of the reception intensity of the radio signal detected by the spectrum analysis section 26.

The outer surface information is generated in step S105 as described below. As has already been described, the magnetic field detectors 6 are arranged on the outer surface of the subject 1. Therefore, position information of the magnetic field detectors 6a to 6h derived in step S104 indicates positions of a part of the outer surface of the subject 1. In the first embodiment, a shape of the outer surface of the subject 1 is derived by connecting the positions of the magnetic field detectors 6a to 6h adjacent to each other with a line to generate a three-dimensional closed surface, and the outer surface information is generated by associating the derived three-dimensional closed surface with each of the magnetic field detectors 6a to 6h. In this regard, more detailed outer surface information can be derived by applying the generated outer surface information to a body template.

Naturally, it is more preferable to use information on the independently existing outer surface sensors 7 when generating the three-dimensional closed surface.

Figure 6:
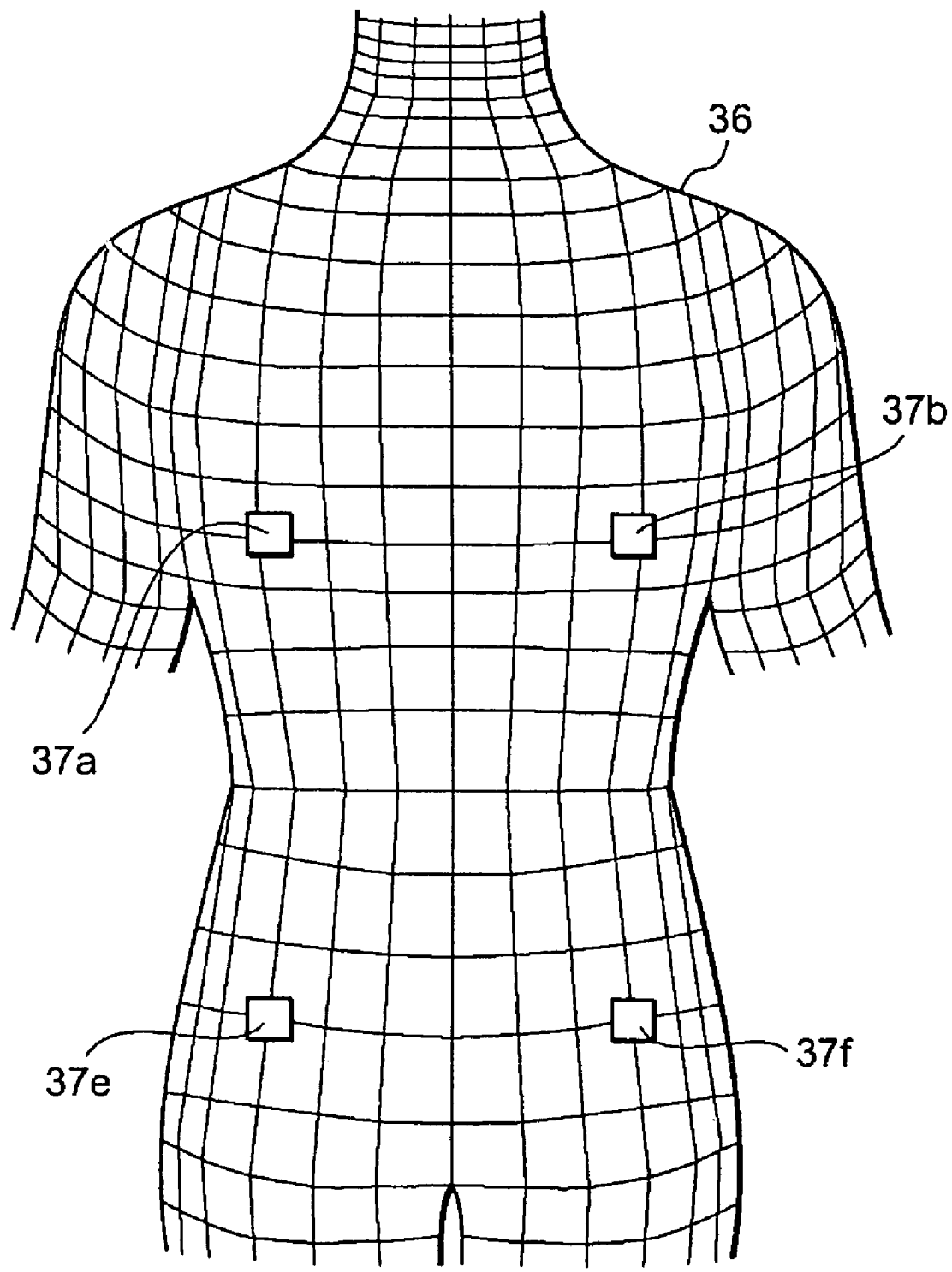
FIG. 6 is a schematic view showing an example of the outer surface information.

Referring to FIG. 6, there is shown a schematic illustration of an example of the outer surface information derived in step S105 as a visual display. In the first embodiment, the outer surface information includes the shape of the outer surface of the subject 1 and the position information of the magnetic field detectors 6a to 6h on the outer surface. Therefore, if the outer surface information is visually displayed, an outer surface image 36 corresponding to the shape of the outer surface of the subject 1 and magnetic field detector images 37a, 37b, 37e, and 37f corresponding to the magnetic field detectors 6a, 6b, 6e, and 6f, respectively, are displayed as shown in FIG. 6. In step S105, the outer surface information is generated visually as shown in FIG. 6. The outer surface information is output to the relative position information deriving device 10 and used to derive the relative position of the test capsule.

Figure 7:
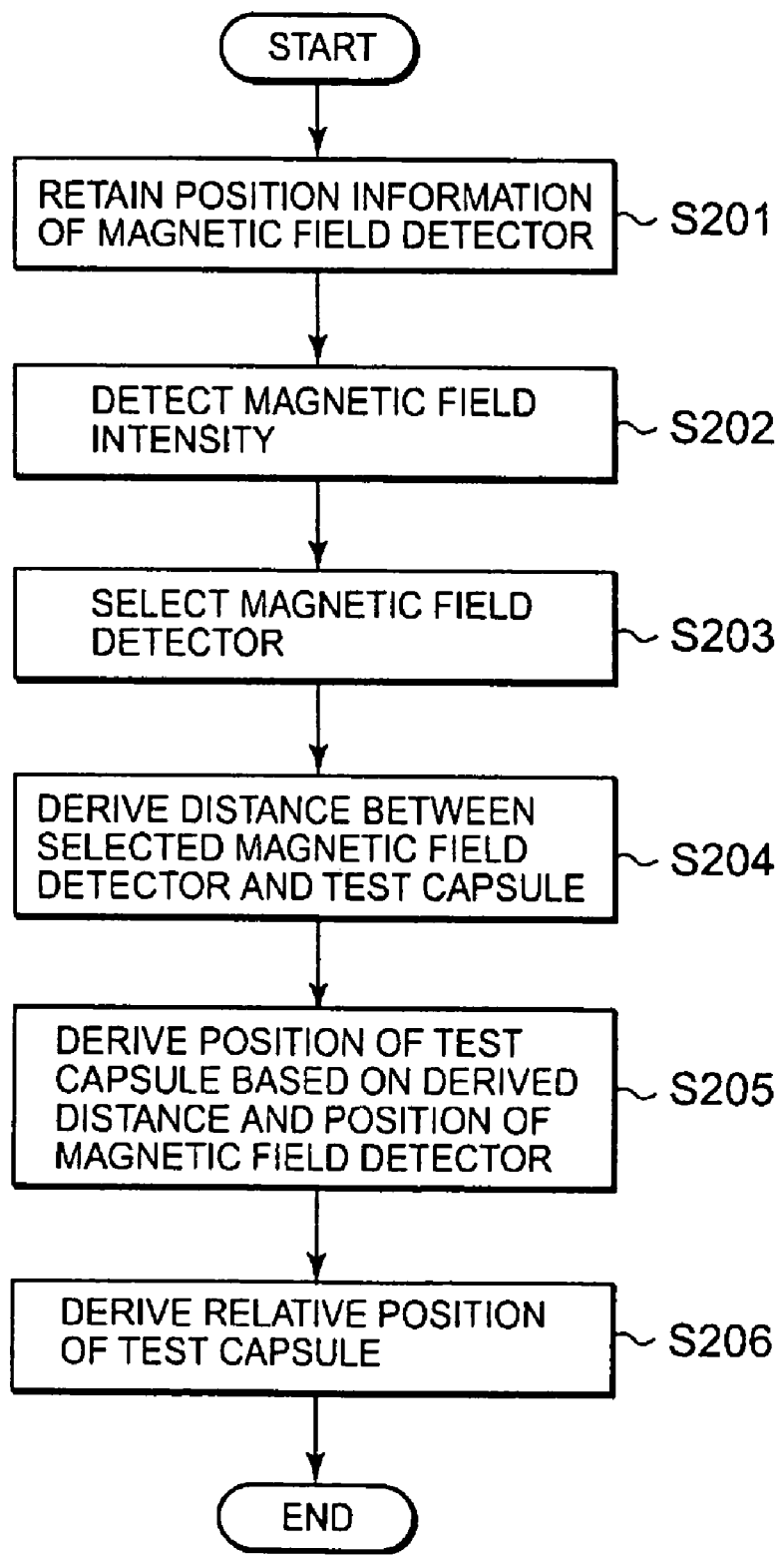
FIG. 7 is a flowchart for explaining an operation of deriving a position of the test capsule relative to an outer surface.

The following describes how the relative position information deriving device 10 derives the relative position of the test capsule 2. Referring to FIG. 7, there is shown a flowchart for explaining how the relative position information deriving device 10 derives the position of the test capsule 2. As shown in FIG. 7, the relative position information deriving device 10 retains the outer surface information derived by the outer surface information deriving device 8 in the outer surface information retaining section 33, first (step S201). The relative position information deriving device 10 then detects intensities of the static magnetic field generated by the permanent magnet 12 included in the test capsule 2 detected by the magnetic field detectors 6a to 6h (step S202) and selects magnetic field detectors 6 on the basis of the detected intensities by means of the selector 31 (step S203).

Thereafter, it derives a distance between each of the selected magnetic field detectors 6 and the test capsule 2 (step S204) and derives the position of the test capsule 2 relative to each of the magnetic field detectors 6 on the basis of the derived distance and the position of the selected magnetic field detector 6 (step S205). The relative position information deriving device 10 then derives the relative position of the test capsule 2 relative to the outer surface of the subject 1 by using the position information to the magnetic field detector 6 obtained in step S205 and the outer surface information retained in the outer surface information retaining section 33 (step S206).

The operation in steps S201 to S206 is repeated for a predetermined time or until the test capsule 2 reaches a predetermined position or is otherwise excreted to the outside of the subject 1, while information on the relative position of the test capsule 2 to the outer surface of the subject 1 at each time is recorded into the portable recording medium 5.

Figure 8:
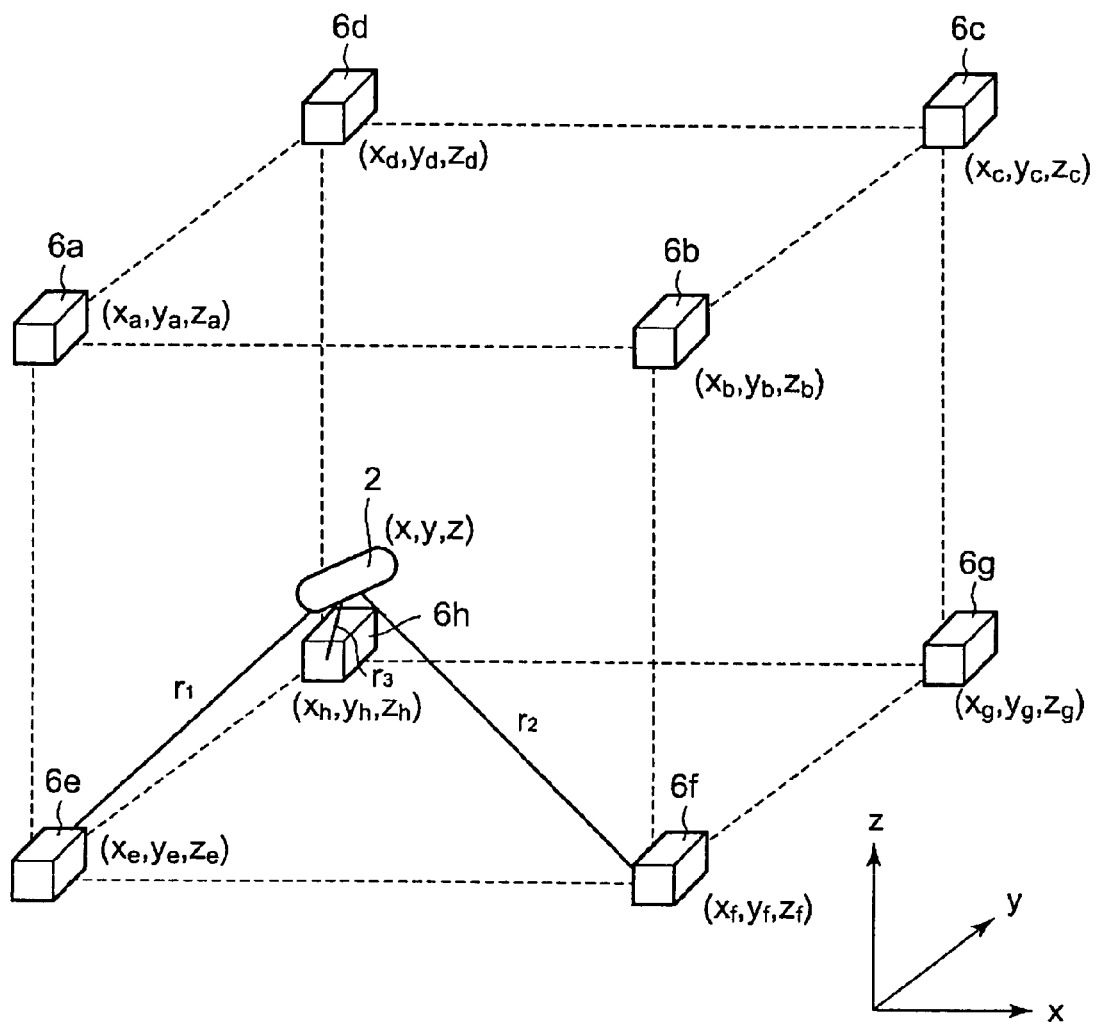
FIG. 8 is a schematic view for explaining a derivation of a position of the test capsule to a magnetic field detector.

The derivation of the position of the test capsule 2 to the magnetic field detector 6 in step S205 is briefly described below. Referring to FIG. 8, there is shown a schematic view for explaining the operation of deriving the position of the test capsule 2 to the magnetic field detector 6. In the following description, it is assumed that all positions of the magnetic field detectors 6a to 6h are derived in the foregoing step S104 and that the positions are represented by coordinates (xa, ya, za) to (xh, yh, zh) as shown in FIG. 8. Moreover, it is assumed that the magnetic field detectors 6e, 6f, and 6h have been selected in step S203 and that distances r1, r2, and r3 between the magnetic field detectors 6e, 6f, and 6h and the test capsule 2 have been derived in step S204.

In this condition, the position coordinates (x, y, z) of the test capsule 2 are derived on the basis of expressions shown below. In other words, the following relational expressions become true on the basis of the coordinates of the magnetic field detectors 6e, 6f, and 6h and the distances r1, r2, and r3:

$$(x-xe)^2+(y-ye)^2+(z-ze)^2=r1^2 \quad (2)$$

$$(x-xf)^2+(y-yf)^2+(z-zf)^2=r2^2 \quad (3)$$

$$(x-xh)^2+(y-yh)^2+(z-zh)^2=r3^2 \quad (4)$$

In the expressions (2) to (4), specific values have been derived for xe, xf, xh, ye, yf, yh, ze, zf, zh and r1, r2, r3 in steps S104 and S204, respectively. Therefore, in step S205, there are three unknowns x, y, and z in the expressions (2) to (4). The position coordinates of the test capsule 2 are derived by solving the unknowns with simultaneous equations of the expressions (2) to (4). The following is a brief description of the derivation of the relative position of the test capsule 2 to the outer surface of the subject 1 performed in step S206. As described above, the outer surface information including the information on the shape of the outer surface and the positions of the magnetic field detectors 6a to 6h to the outer surface is generated by processing in steps S101 to S106. On the other hand, in step S205, positional relations between selected ones out of the magnetic field detectors 6a to 6h and the test capsule 2 are derived. Therefore, the positional relation between the outer surface of the subject 1 and the test capsule 2 is uniquely defined through the position information of the magnetic field detectors 6a to 6h. Accordingly, it becomes possible to derive the relative position of the test capsule 2 to the outer surface of the subject 1 by using the information.

Figure 9:
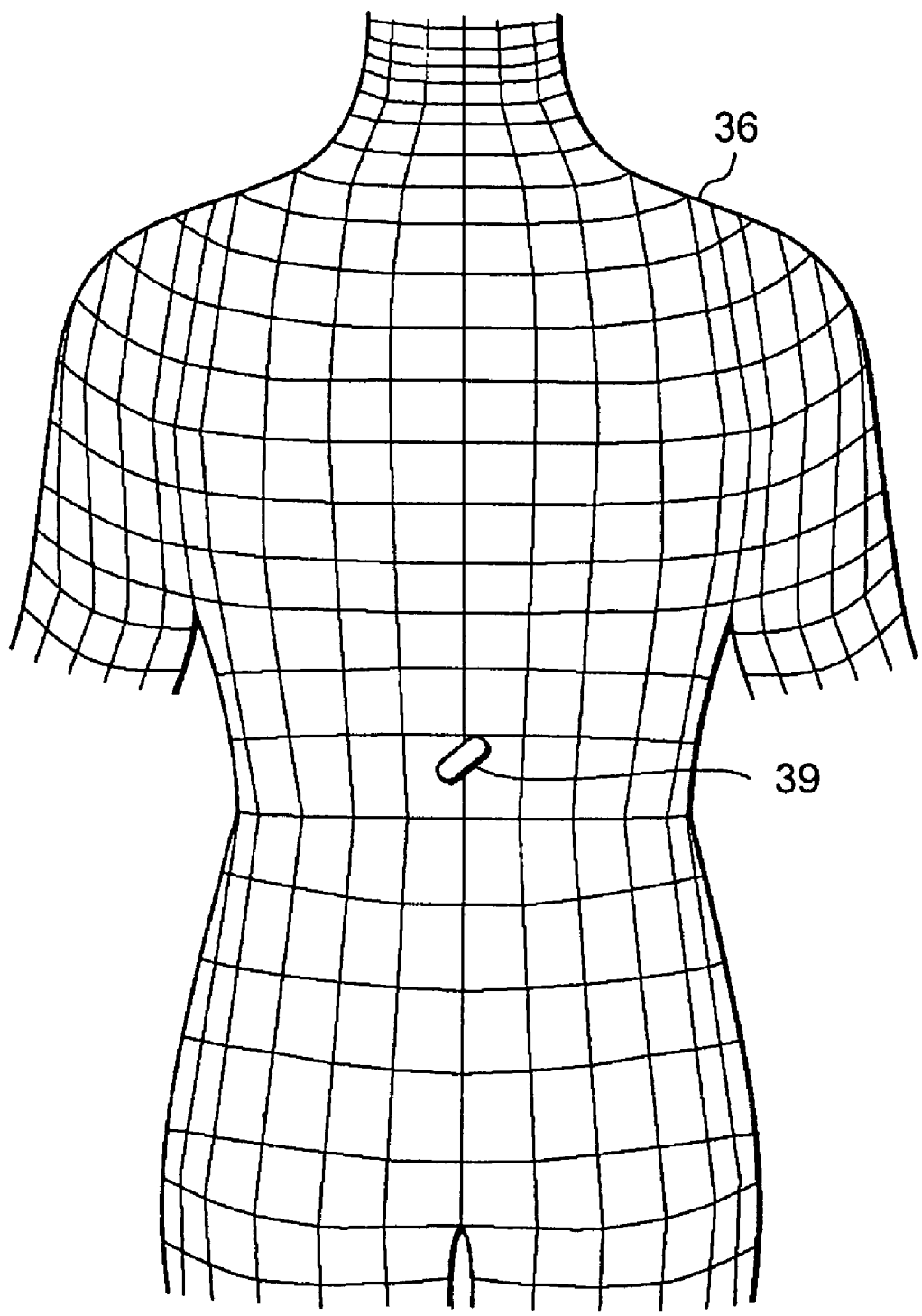
FIG. 9 is a schematic view showing an example of an image displayed by a display device.

FIG. 9 is a schematic illustration showing the relative position relationship between the outer surface of the subject 1 and the test capsule 2 derived based on the above algorithm. In step S206, information visually shown in FIG. 9 is generated. The display device 4 displays the relative position of the test capsule 2 to the outer surface of the subject 1 by acquiring information visually shown in FIG. 9 via the portable recording medium 5. Specifically, as shown in FIG. 9, the display device 4 displays an outer surface image 36 included in the outer surface information derived in steps S101 to S105 and a capsule image 39 corresponding to the relative position of the test capsule 2 derived in step S206. These images are displayed on a screen of the display device 4, by which the relative position of the test capsule 2 to the outer surface of the subject 1 is displayed.

Subsequently, advantages of the intra-subject position display system according to the first embodiment will be described below. First, in the intra-subject position display system according to the first embodiment, the position of the test capsule 2 is displayed so as to correspond to an area in the outer surface of the subject 1 into which the test capsule 2 is introduced. Therefore, by using the intra-subject position display system according to the first embodiment, a doctor, a nurse, or the like can visually grasp the relative position of the test capsule 2 relative to the outer surface of the subject 1. Thus, the doctor, the nurse, or the like can not only recognize the position coordinates of the test capsule 2, but can easily determine approximately which inside area of the subject 1 the test capsule 2 is located. Particularly, the doctor; the nurse, or the like generally has a knowledge such as what organ exists in which area in the inside of the subject 1. Therefore, it is possible to easily acquire information such as which organ in the inside of the subject 1 the test capsule 2 is passing through by displaying the position of the test capsule 2 to the outer surface of the subject 1. Therefore, the intra-subject position display system according to the first embodiment has an advantage that the doctor, the nurse, or the like can rapidly make a diagnosis of the organ the test capsule 2 is hard to pass through when the traveling speed of the test capsule 2 decreases.

Moreover, in the intra-subject position display system according to the first embodiment, the outer surface information, which is information on the shape or the like of the outer surface of the subject 1, is generated every time the test capsule 2 is used. Therefore, the intra-subject position display system has an advantage that it is possible to acquire an outer surface image corresponding to a difference in a build of the subject's body caused by individual variations of the subject 1 such as, for example, sex, age, race, or the like, thereby achieving a more accurate relative position of the test capsule 2.

Moreover, the intra-subject position display system according to the first embodiment has a feature of repeating the derivation of the outer surface information and the derivation of the position of the test capsule 2 until the test capsule 2 is excreted and of deriving the respective positions of the test capsule 2 relative to the outer surface sequentially during the time. Therefore, even if an absolute position of the test capsule 2 changes discontinuously due to a change in the posture or the like of the subject 1, it is possible to easily grasp the position of the test capsule 2 in the inside of the subject 1 by perceiving the outer surface image of the subject 1 that has changed in the posture or the like.

The intra-subject position display system according to the first embodiment has the permanent magnet 12 in the test capsule 2 and has a feature of detecting the position of the test capsule 2 in the inside of the subject 1 on the basis of the detected intensity of the static magnetic field generated by the permanent magnet 12. Naturally, the position of the test capsule can be detected by using an electromagnetic wave instead of the magnetic field. If the electromagnetic wave is used, however, specific inductive capacity or conductivity values of organs are varied, by which an extinction ratio of the radio signal intensity varies greatly according to a type of component. For example, if the liver or blood vessel exists, radio signals are absorbed in a large quantity and thereby the extinction ratio increases, which prevents the detection of an accurate position. Unlike the electromagnetic wave, the static magnetic field has a characteristic that the intensity substantially uniquely attenuates independently of a change in physical parameters such as a specific inductive capacity and a magnetic permeability in a propagation region thereby favorably achieving the relation expressed by the equation (1). Therefore, the static magnetic field has an advantage of enabling a position detection at a high accuracy in comparison with a position detection with an electromagnetic wave or the like even in detecting a position in a space where organs different in physical parameters from one another like an inside of the human body.

An example of another advantage of the use of a static magnetic field, is the same results in a reduction in load on the subject 1 when the test capsule 2 is introduced into the subject 1. In other words, for the reasons mentioned above, the intra-subject position display system according to the first embodiment has an advantage of suppressing the decrease in an accuracy of the detected position caused by a difference in a surrounding environment of the test capsule 2. Therefore, for example, when the test capsule 2 is introduced into the subject, there is no need for a restriction such as refraining from eating or drinking as has been needed in other test methods. Accordingly, the subject 1 can lead a normal life during the test with the test capsule 2, thereby reducing a load on the subject 1 during the test.

Moreover, the intra-subject position display system according to the first embodiment comprises the outer surface information deriving device 8 for deriving the positions of the magnetic field detectors 6a to 6h for detecting intensities of the static magnetic field generated by the test capsule 2. As has been mentioned above; the magnetic field detectors 6a to 6h are arranged on the outer surface of the subject 1. Therefore, due to a divergence of position over time or a difference in position caused by a change in the posture of the subject 1 or the like, the respective positions of the magnetic field detectors 6a to 6h change relative to the subject 1. Accordingly, the outer surface information deriving device 8 actually derives the positions of the magnetic field detectors 6a to 6h and derives the position of the test capsule 2 by using the derived positions, thereby enabling an accurate derivation of the position of the test capsule is 2 independently of any change in the posture of the subject 1.

In addition, the intra-subject position display system according to the first embodiment uses a radio signal for deriving the positions of the magnetic field detectors 6a to 6h and derives the positions in a different mode from the static magnetic field used for deriving the position of the test capsule 2. The transmission of the radio signal and that of the static magnetic field are independent of each other without any interference therebetween. Therefore, the intra-subject position display system according to the first embodiment is capable of preventing the position derivation of the magnetic field detectors 6a to 6h from adversely affecting the position derivation of the test capsule 2. Thus, the intra-subject position display system according to the first embodiment has an advantage of being capable of deriving the positions of the magnetic field detectors 6a to 6h without affecting the position derivation of the test capsule 2 even after the test capsule 2 is introduced into the subject 1.

While a radio signal has been used for deriving the positions of the magnetic field detectors 6a to 6h, the difference in the extinction ratio or the like caused by internal organs of the subject 1 will be negligible and have substantially no effect, unlike the position derivation of the test capsule. In other words, unlike the test capsule moving in a wide range from the esophagus to the colon, the position range of the magnetic field detectors 6a to 6h is not so large, though a change in the posture of the subject 1 will cause their position changes. Moreover, the internal organs existing between the magnetic field detectors 6a to 6h and the outer surface information deriving device 8 do not change significantly with the change in the positions. For example, by using a structure of comparing intensities of radio signals transmitted from the magnetic field detectors 6a to 6h in the initial state with intensities of radio signals at detecting the positions, it is possible to reduce an error in a derived position caused by the difference in the extinction ratio.

The following is a description of an intra-subject position display system according to a second embodiment. The intra-subject position display system according to the second embodiment comprises an RFID tag as a second radio section included in an outer surface sensor section so as to be capable of identifying a transmission source of a radio signal transmitted from a plurality of outer surface sensors 7 arranged on an outer surface of a subject 1. The intra-subject position display system according to the second embodiment has the same configuration as the first embodiment except the outer surface sensor section and an outer surface information deriving device, and therefore the illustration and description for the same parts will be omitted hereinafter.

Figure 10:
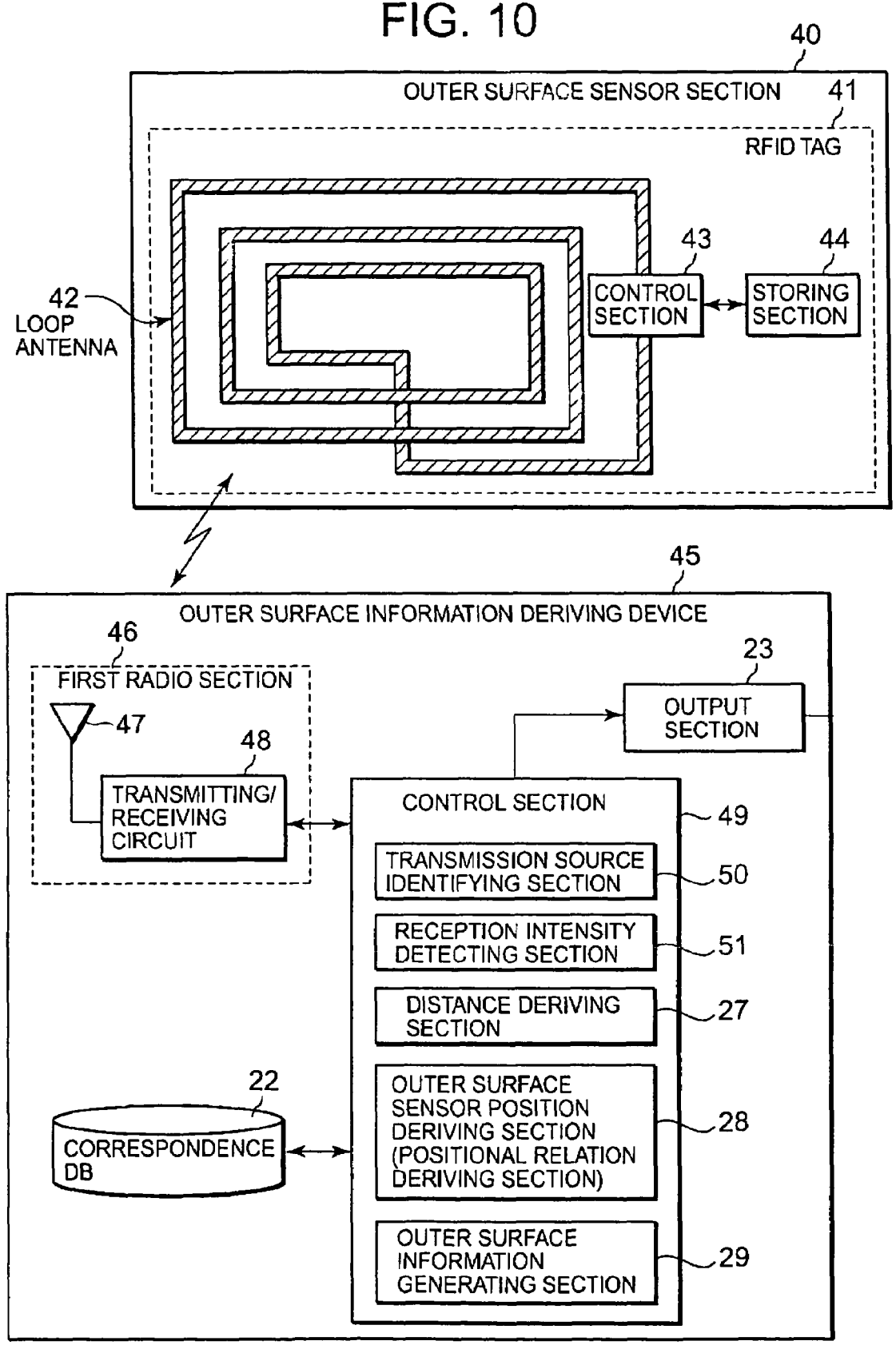
FIG. 10 is a schematic view showing a configuration of an outer surface sensor section and of an outer surface information deriving device provided in an intra-subject position display system according to a second embodiment.

Referring to FIG. 10, there is shown a schematic view of a specific configuration of the outer surface sensor section and the outer surface information deriving device included in the intra-subject position display system according to the second embodiment. As shown in FIG. 10, the outer surface sensor section 40 includes an RFID tag 41 as a second radio section. The RFID tag 41 specifically includes a control section 43 connected to a loop antenna 42 and a storing section 44 having a function of outputting at least storage information to the control section 43 on the basis of an instruction from the control section 43.

The loop antenna 42 is for use in receiving a radio signal transmitted from the side of the outer surface information deriving device and including a control signal and a power supply signal. Specifically, the loop antenna 42 has a function of receiving the radio signal transmitted from the side of the outer surface information deriving device 45 and outputting it to the control section 43. On the other hand, the control section 43 extracts a power supply signal and a control signal from the radio signal, generates a driving power on the basis of the power supply signal, and instructs the storing section 44 to output stored information on the basis of the control signal. In response to this, the storing section 44 stores identification information different from other identification information on each of the plurality of outer surface sensors 7 and outputs the identification information to the control section 43. The control section 43 generates a given radio signal including the acquired identification information and transmits it to an outer surface information deriving device 45 via the loop antenna 42.

In response to the arrangement of the RFID tag 41 in the outer surface sensor section 40, the outer surface information deriving device 45 includes a transmitting/receiving antenna 47 and a transmitting/receiving circuit 48 in a first radio section 46 and includes a transmission source identifying section 50 and a reception intensity detecting section 51 in the control section 49. The provision of the new transmission function of the first radio section 46 is based on the need for transmitting a radio signal for driving the RFID tag 41. The transmission source identifying section 50 in the control section 49 is for use in identifying the outer surface sensor 7 from which the radio signal has been transmitted by decoding identification information included in the radio signal transmitted from the RFID tag 41. The reception intensity detecting section 51 is for use in detecting the reception intensity of the radio signal whose transmission source has been identified.

In this manner, if the RFID tag 41 is used as a second radio section, the transmission source can be identified by using the identification information included in the radio signal. Therefore, the intra-subject position display system according to the second embodiment has an advantage of enabling a system configuration with a simple structure without a need for different settings of frequencies of radio signals transmitted from the outer surface sensors 7.

The following is a description of an intra-subject position display system according to a third embodiment. The intra-subject position display system according to the third embodiment, having a plurality of reference positions and more preferably three or more positions, comprises a reference sensor having a plurality of receiving antennas in response to the reference positions. In the intra-subject position display system according to the third embodiment, composing elements other than the reference sensor are the same as those in the first and second embodiments. Therefore, their illustration and description will be omitted hereinafter.

Figure 11:
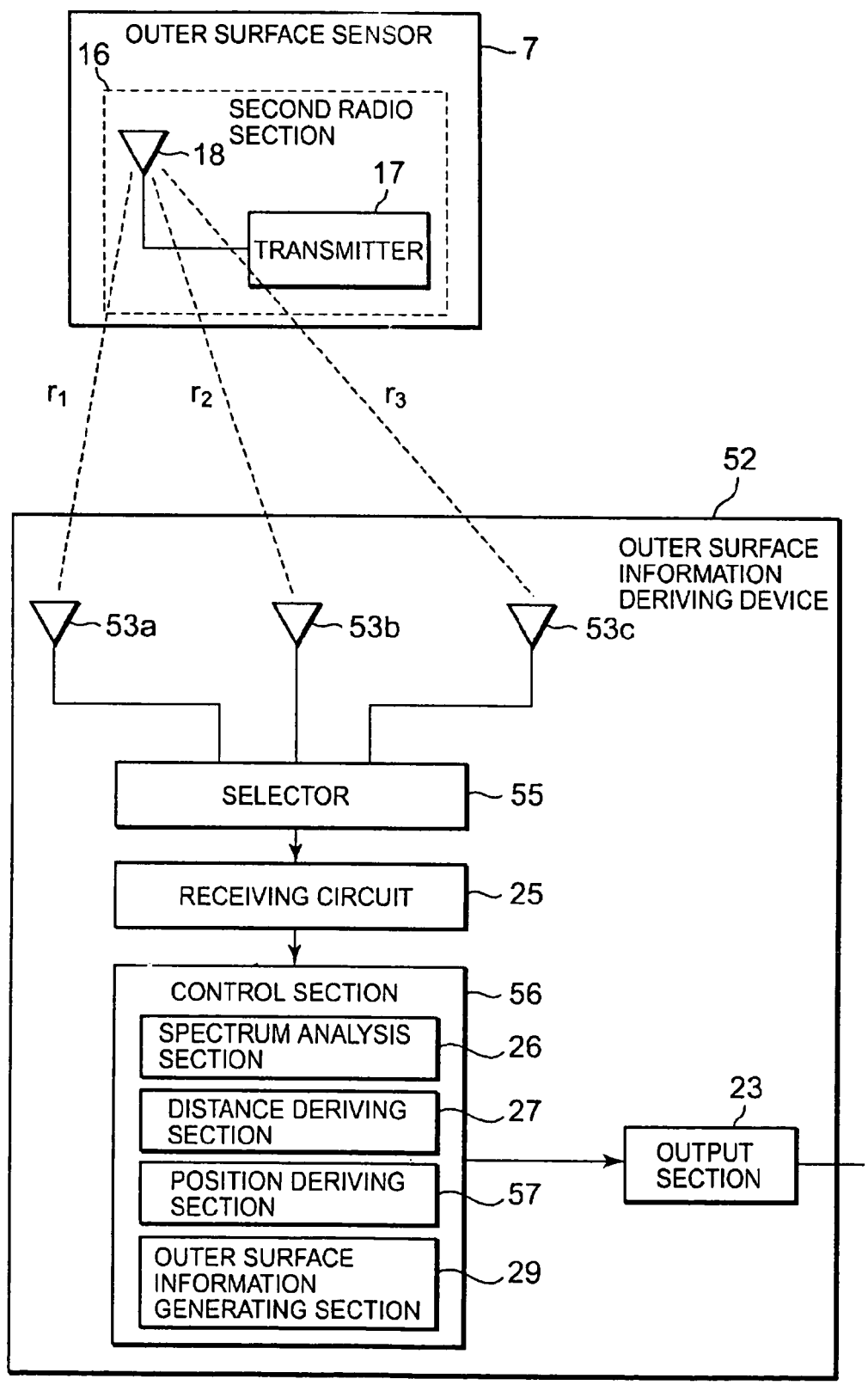
FIG. 11 is a schematic view showing a configuration of an outer surface sensor and of an outer surface information deriving device provided in an intra-subject position display system according to a third embodiment.

Referring to FIG. 11, there is shown a block diagram of a configuration and functions of the intra-subject position display system according to the third embodiment. As shown in FIG. 11, a reference outer surface information deriving device 52 includes receiving antennas 53a to 53c arranged in response to the plurality of reference positions and a selector 55 between the receiving antennas 53a to 53c and the receiving circuit 25. A control section 56 includes a position deriving section 57 for deriving a position according to an algorithm different from that of the outer surface sensor position deriving section 28 in the first and second embodiments.

A position deriving operation of the outer surface sensor 7 in the third embodiment will be briefly described below. In the third embodiment, radio signals transmitted form the outer surface sensor 7 are received via the receiving antennas 53a to 53c and the selector 55 sequentially outputs the radio signals received via the receiving antennas 53a to 53c to the receiving circuit 25. The receiving circuit 25 outputs the radio signals to the control section 56 after conducting decoding or other processing for each of the radio signals. A distance deriving section 27 included in the control section 56 derives distances ra, rb, and rc between the plurality of reference positions and the outer surface sensor 7.

Subsequently, an operation of the position deriving section 57 will be described below. The position deriving section 57 previously receives specific position coordinates of the plurality of reference positions corresponding to the receiving antennas 53a to 53c and derives a position of the outer surface sensor 7 on the basis of the position coordinates of the receiving antennas 53a to 53c and the distances r1, r2, and r3 between the receiving antennas 53a to 53c and the outer surface sensor 7. Specifically, assuming that the position coordinates of the receiving antennas 53a to 53c are (x1, y1, z1), (x2, y2, z2), and (x3, y3, z3) and that the position coordinates of the magnetic field detector 6 to be derived are (x, y, z), the following equations are true:

$$(x-x1)2+(y-y1)2+(z-Z1)2=r1^2 \quad (5)$$

$$(x-x2)2+(y-y2)2+(z-Z2)2=r3^2 \quad (6)$$

$$(x-x3)2+(y-y3)2+(z-Z3)2=r3^2 \quad (7)$$

Since unknowns in the equations (5) to (7) are x, y, and z, a specific position of the outer surface sensor 7 is derived by solving the equations (5) to (7).

With deriving the position of the outer surface sensor 7 in this mode, the intra-subject position display system according to the third embodiment can derive the position of the outer surface sensor 7 without a correspondence database. Moreover, the reference outer surface information deriving device 52 has a function of deriving a position on the basis of only radio signals received by the plurality of receiving antennas 53a to 53c without a correspondence previously derived in a stereotyped manner. Therefore, it can derive the position of the outer surface sensor 7 more accurately in response to individual variations or the like of the operation of the subject 1. As a result, the intra-subject position display system has an advantage of being capable of deriving the relative position of the test capsule 2 with a high accuracy.

Subsequently, an intra-subject position display system according to a fourth embodiment will be described below. In the intra-subject position display system according to the fourth embodiment, an outer surface information deriving device not only detects intensities of radio signals transmitted from outer surface sensors 7, but also detects directions of transmission sources. In the intra-subject position display system according to the fourth embodiment, composing elements other than a reference sensor are the same as those in the first and second embodiments. Therefore, their illustration and description is omitted hereinafter.

Figure 12:
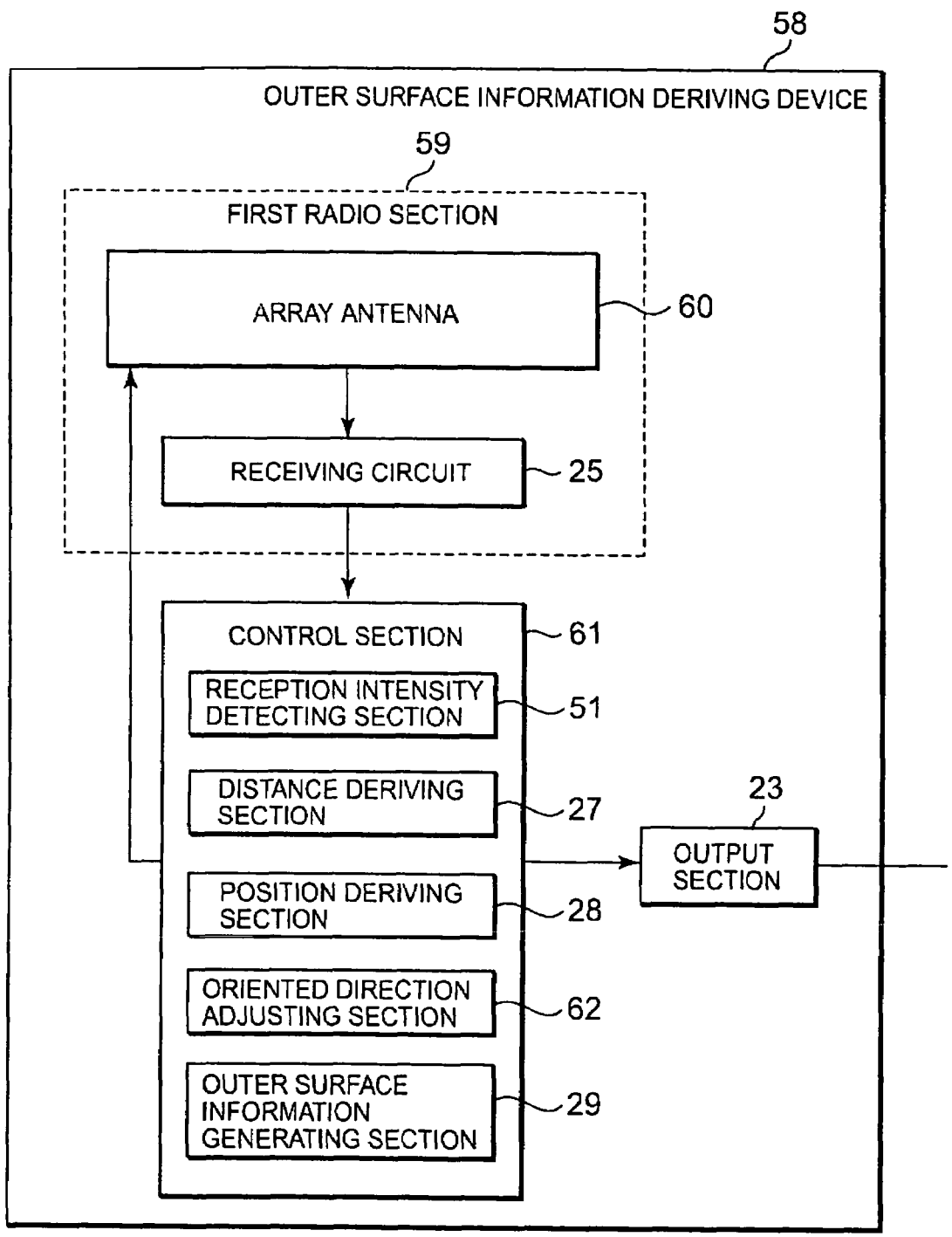
FIG. 12 is a schematic view showing a configuration of an outer surface information deriving device provided in an intra-subject position display system according to a fourth embodiment.

Referring to FIG. 12, there is shown a block diagram of a configuration of the intra-subject position display system according to the fourth embodiment. As shown in FIG. 12, an outer surface information deriving device 58 includes a first radio section 59 having an array antenna 60 instead of the receiving antenna 24 in the first embodiment, a control section 61 having an oriented direction adjusting section 62, and an output section 23.

When receiving radio signals transmitted from the outer surface sensors 7, the array antenna 60 detects also a direction in which each of the outer surface sensors 7 as a transmission source is located. Specifically, the array antenna 60 includes a plurality of receiving antennas arranged in a form of, for example, a two-dimensional matrix and a signal processing mechanism for giving high receiving sensitivities in a given direction (hereinafter, referred to as "oriented direction") to the entire array antenna 60 by amplifying, delaying, or otherwise processing radio signals received by the receiving antennas. The oriented direction adjusting section 62 in the control section 61 has a function of changing the oriented direction of the array antenna 60 over a given range.

The following is a description of deriving a position of a magnetic field detector 6 in the intra-subject position display system according to the fourth embodiment. First, the outer surface information deriving device 58 searches for directions in which the array antenna 60 can receive radio signals transmitted from the outer surface sensors 7 while adjusting the oriented direction of the array antenna 60 by means of the oriented direction adjusting section 62. Thereafter, when the oriented direction controlled by the oriented direction adjusting section 62 matches the direction in which the outer surface sensor 7 is located, the radio signal is received via the array antenna 60 and a reception intensity of the radio signal received by a reception intensity detecting section 51 is detected. At that time, a distance deriving section 27 derives a distance between a reference position where the array antenna 60 is disposed and the outer surface sensor 7 on the basis of the detected reception intensity and then information on the distance is transmitted to the outer surface sensor position deriving section 28.

On the other hand, the outer surface sensor position deriving section 28 acquires information on the oriented direction at receiving the radio signal from the oriented direction adjusting section 62. In other words, the oriented direction in which the radio signal from the magnetic field detector 6 is received matches the direction in which the outer surface sensor 7 is located, and therefore the outer surface sensor position deriving section 28 derives the position of the outer surface sensor 7 on the basis of the oriented direction and the distance derived by the distance driving section 27. While the position of the magnetic field detector 6 derived in this process is represented by three-dimensional polar coordinates, the outer surface sensor position deriving section 28 can convert it to a three-dimensional rectangular coordinate system and output it via the output section 23.

In the intra-subject position display system according to the fourth embodiment, the position of the outer surface sensor 7 is derived by directly detecting the distance between the reference position and the outer surface sensor 7 and the direction in which the outer surface sensor 7 is located. Therefore, the intra-subject position display system according to the fourth embodiment can derive the position of the outer surface sensor 7 is without complicated calculations.

Subsequently, an intra-subject position display system according to a fifth embodiment will be described below. In the intra-subject position display system according to the fifth embodiment, a capsule type endoscope is used as an intra-subject device and a relative position information deriving device has a function of processing a radio signal transmitted from the capsule type endoscope.

Figure 13:
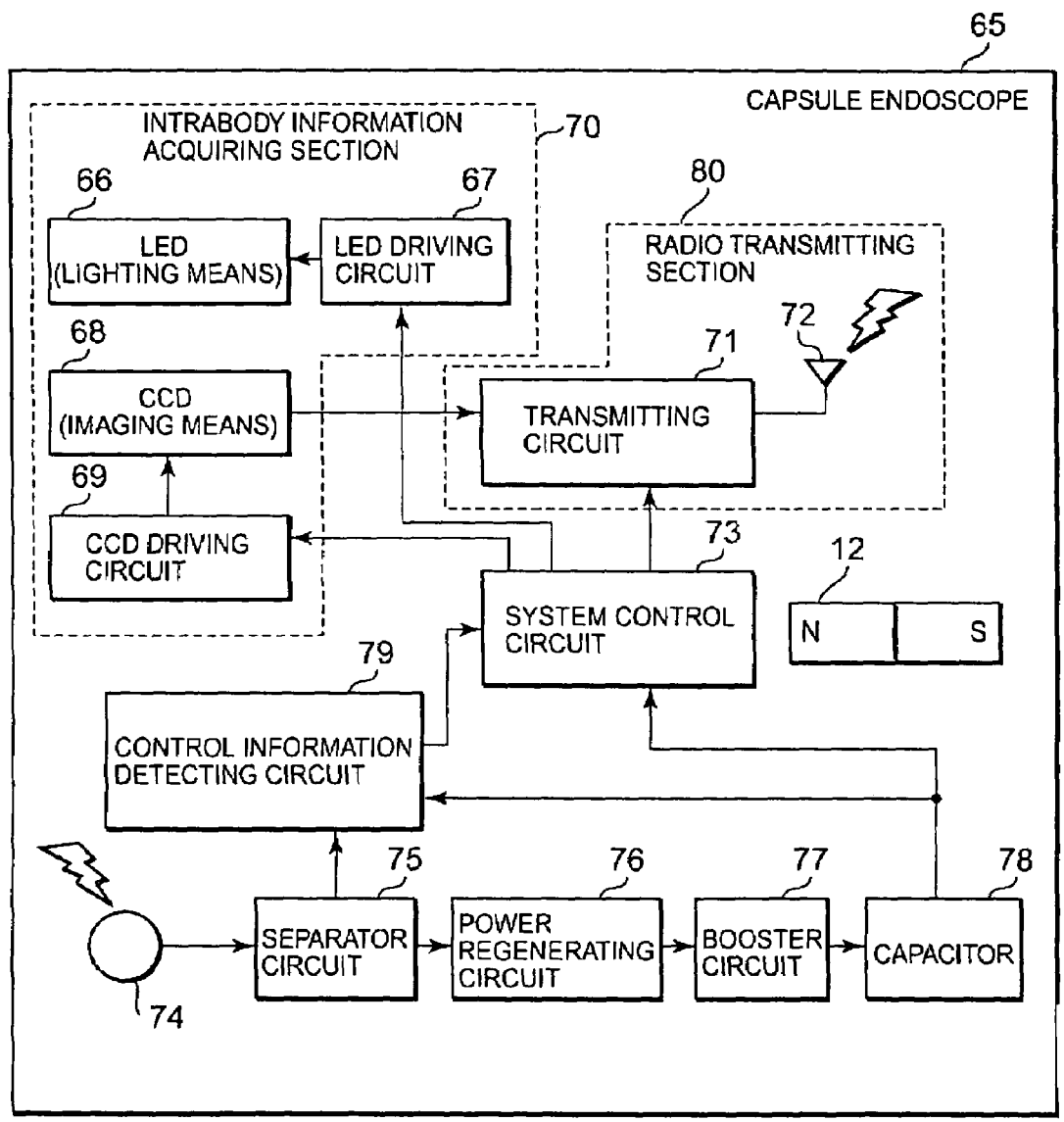
FIG. 13 is a block diagram showing a configuration of a capsule type endoscope in an intra-subject position display system according to a fifth embodiment.
Figure 14:
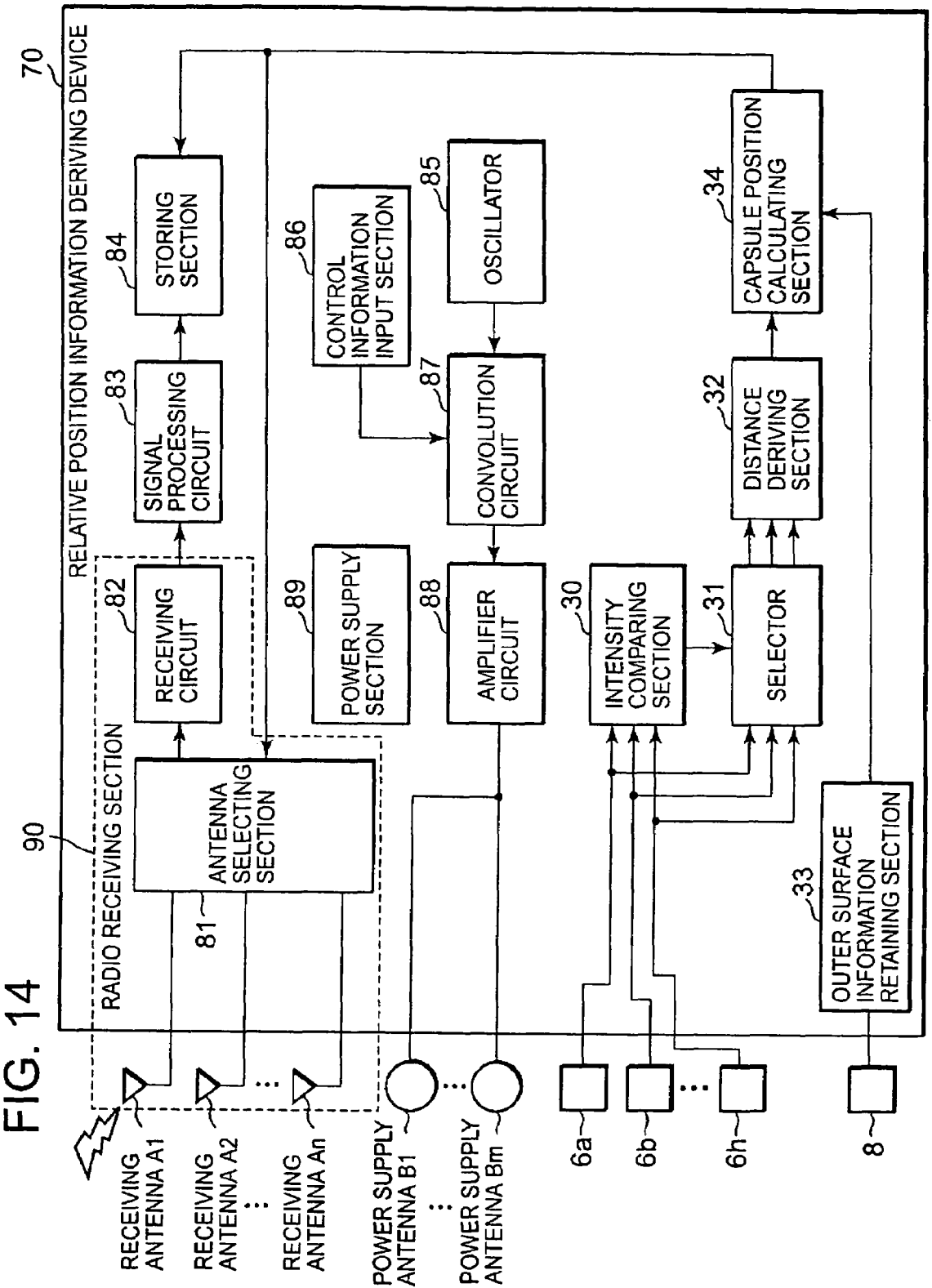
FIG. 14 is a block diagram showing a configuration of a relative position information deriving device provided in the intra-subject position display system according to the fourth embodiment

FIG. 13 is a block diagram showing a configuration of the capsule type endoscope used as an example of the intra-subject device in the fifth embodiment. Although the capsule type endoscope is shown schematically in the block diagram of FIG. 14 as rectangular in shape, the same is assumed to have a shape similar to that of the test capsule 2 discussed above. FIG. 14 is a block diagram showing a configuration of the relative position information deriving device included in the intra-subject position display system. In the fifth embodiment, composing elements other than the capsule type endoscope and the relative position information deriving device are the same as those in the first to fourth embodiments. Therefore, their illustration and description will be omitted hereinafter.

As shown in FIG. 13, a capsule type endoscope 65 includes, a permanent magnet 12, an LED 66 functioning as a lighting section for irradiating an imaging area and taking an image of an inside of the subject 1, an LED driving circuit 67 for controlling a driven state of the LED 66, a CCD 68 functioning as an imaging section that takes a reflected light image from the area irradiated by the LED 66, and a CCD driving circuit 69 for controlling a driven state of the CCD 68. The LED 66, the LED driving circuit 67, the CCD 68, and the CCD driving circuit 69 function as an intra-subject information acquiring section 70 as a whole.

The capsule type endoscope 65 includes a transmitting circuit 71 for modulating image data taken by the CCD 68 and generating an RF signal, a transmitting antenna section 72 as a radio section for wirelessly transmitting the RF signal output from the transmitting circuit 71, the LED driving circuit 67, the CCD driving circuit 69, and a system control circuit 73 for controlling an operation of the transmitting circuit 71. The transmitting circuit 71 and the transmitting antenna section 72 function as a radio transmitting section 80 as a whole.

With these features, the capsule type endoscope 65 acquires image data of the subject site irradiated by the LED 66 by means of the CCD 68 while it is introduced into the subject 1. The acquired image data is converted to an RF signal in the transmitting circuit 71 and then transmitted to an outside via the transmitting antenna section 72.

Moreover, the capsule type endoscope 65 has a feature for receiving a radio signal transmitted from the relative position information deriving device 70 positioned outside the subject 1. Specifically, the capsule type endoscope 65 includes a receiving antenna section 74 for receiving the radio signal transmitted from the side of the relative position information deriving device 70 and a separator circuit 75 for separating a power supply signal from the radio signal received by the receiving antenna section 74. Furthermore, the capsule type endoscope 65 includes a power regenerating circuit 76 for regenerating power from the separated power supply signal, a booster circuit-77 for boosting the regenerated power, and a capacitor 78 for storing the boosted power. Still further, the capsule type endoscope 65 includes a control information detecting circuit 79 for detecting a content of a control information signal from the remaining component of the radio signal from which the power supply signal has been separated by the separator circuit 75 and outputs the detected control information signal to the system control circuit 73.

With these features, the capsule type endoscope 65 receives the radio signal transmitted from the side of the relative position information deriving device 70 at the receiving antenna section 74, first, and separates the power supply signal and the control information signal from the received radio signal by means of the separator circuit 75.

The control information signal separated by the separator circuit 75 is input to the system control circuit 73 via the control information detecting circuit 79. The system control circuit 73 controls driven states of the LED 66, the CCD 68, and the transmitting circuit 71 on the basis of moving state information. On the other hand, the power supply signal is regenerated as power by the power generating circuit 76 and the regenerated power is boosted to a potential suitable for the capacitor 78 by the booster circuit 77. Thereafter, the power is stored in the capacitor 78.

Subsequently, a position detector in this embodiment will be described with reference to FIG. 14. As shown in FIG. 14, the position detector includes receiving antennas A1 to An and power supply antennas B1 to Bm in addition to the features of the first to fourth embodiments and has a function of a receiver for receiving a radio signal transmitted from the capsule type endoscope 65 and a function of a transmitter for wirelessly transmitting a given signal to the capsule type endoscope 65.

First, the relative position information deriving device 70 has a feature of a receiver for receiving image data of the inside of a subject 1 having been wirelessly transmitted from the capsule type endoscope 65. Specifically, the relative position information deriving device 70 includes a receiving circuit 82 for performing given processing such as demodulation for a radio signal received by a selected receiving antenna and extracting image data acquired by the capsule type endoscope 65 from the radio signal, a signal processing circuit 83 for performing processing necessary for output image data, and a storing section 84 for recording image-processed image data or the like.

The storing section 84 has a function of storing image data and further has a function of storing position information of the capsule type endoscope 65 derived by a capsule position calculating section 34. With these features, a display device 4 can display an image of the subject 1 and the position in the subject 1 where the image has been picked up simultaneously.

Furthermore, the relative position information deriving device 70 has a feature of a transmitter for generating a power supply signal and a control information signal transmitted to the capsule type endoscope 65 and outputting them to the power supply antennas B1 to Bm. Specifically, as shown in FIG. 3, the relative position information deriving device 70 includes an oscillator 85 having a function of generating a power supply signal and a function of regulating an oscillating frequency, a control information input section 86 for generating a control information signal described later, a convolution circuit 87 for combining the power supply signal with the control information signal, and an amplifier circuit 88 for amplifying an intensity of the combined signal. The signal amplified by the amplifier circuit 88 is sent to the power supply antennas B1 to Bm and then transmitted to the capsule type endoscope 65. The relative position information deriving device 70 includes a power supply section 89 including a given capacitor or AC adapter and composing elements of the relative position information deriving device 70 use power as driving energy supplied from the power supply section 89.

With these features, in the intra-subject position display system according to the fifth embodiment, the display device 4 can display not only the relative position of the capsule type endoscope 65, which is one mode of the intra-subject device to the outer surface of the subject 1, but also the intra-subject image taken by the capsule type endoscope 65 in the displayed relative position. Thereby, the intra-subject position display system has an advantage such that a doctor, a nurse, or the like can easily understand the position of the capsule type endoscope relative to the outer surface of the subject 1 in which the intra-subject image has been taken and thus can easily determine which taken image corresponds to which internal organ.

While the present invention has been described according to the first to fifth embodiments hereinabove, it is not limited to them. To the contrary, those skilled in the art can think of various modes, modification, and applications. For example, while the display device 4 displays visual information shown in FIG. 9 in the first embodiment, the interpretation need not be limited to the display mode, but the display device 4 may display, for example, character information which displays a relative position between the outer surface of the subject 1 and the test capsule 2 or other intra-subject device.

While the intra-subject device includes the capsule type endoscope and the test capsule, it is not limited to such intra-subject devices as will be discussed below.

Furthermore, in the first to fifth embodiments, the position detector and the display device 4 are separately formed so as to be independent of each other as shown in FIG. 1. There is no need, however, for limiting the interpretation of the present invention to this arrangement, but the position detector can be integrated with the display device 4. Still further, in the first to fifth embodiments, the second radio section is disposed in the outer surface information deriving device, and the outer surface information deriving device and the relative position information driving device are separately formed so as to be independent of each other. Such features, need not be limited to those disclosed. For example, the relative position information deriving device can be integrated with the outer surface information deriving device and the second radio section and the outer surface information deriving device can be separately formed so as to be independent of each other. Moreover, for example, the correspondence database 22, the outer surface information retaining section 33, and the storing section 35 are treated as separate and independent composing elements for simplifying the description in the embodiments. Such composing elements common in function can be integrated with each other.

Furthermore, in the first to fifth embodiments, some outer surface sensors 7 are built in the magnetic field detectors 6a to 6h, respectively, and other outer surface sensor 7 are separately arranged on the outer surface of the subject 1. Such a feature, however, has been applied for reasons that the number of outer surface sensors 7 need be increased to acquire more accurate outer surface information while three magnetic field sensors 15 should be theoretically enough as the number of magnetic field sensors 15 necessary for detecting a position of the test capsule 2 or the like. Therefore, for example, it is possible to arrange a plurality of magnetic field detectors 6 each having the magnetic field sensor 15 integrated with the outer surface sensor 7 or to apply a simple arrangement only with outer surface sensors 7 built in magnetic field detectors 6a to 6h to derive outer surface information.

Furthermore, for a further simpler arrangement, existing outer surface information can be used to derive and display the relative position of the intra-subject device. A feature of the present invention is to display the position of the intra-subject device relative to the outer surface or other anatomy of the subject. Therefore, a means for performing the display can be in a mode other than the foregoing embodiments. For example, a virtual image of the intra-subject device can be displayed in a see-through head mount display, through which an operator can directly see the outer surface of the subject, to let the operator know the current position of the device. Further, the subject's anatomy image from a previous CAT-scan can over-imposed on the head mount display screen.

Still further, in the fifth embodiment, the intra-subject information acquiring section 70 has been described as one having the CCD 58 as an imaging section and an LED 51 as a lighting section. The intra-subject information acquiring section can be provided with a feature for acquiring information on a pH or a temperature in the subject 1. Moreover, as a feature of the intra-subject device having an oscillator, an ultrasound image in the subject 1 can be acquired. Still further, the present invention can include a feature of acquiring a plurality of types of information from the above information in the subject.

While there has been shown and described what are considered to be preferred embodiments of the invention, it will, of course, be understood that various modifications and changes in form or detail could readily be made without departing from the spirit of the invention. It is therefore intended that the invention not be limited to the exact forms described and illustrated, but constructed to cover all modifications that may fall within the scope of the appended claims.

What is claimed is:

1. An intra-subject position display system for displaying a position of an intra-subject device, which is introduced into a subject and moves therein, the intra-subject position display system comprising:
   a plurality of outer surface sensors configured for arrangement on an outer surface of the subject;
   an outer surface information deriving section for deriving outer surface information including information on the shape of the outer surface of the subject based on positions of the outer surface sensors determined from a signal associated with each of the plurality of outer surface sensors;
   a position detector for detecting a position of the intra-subject device; and a relative position information deriving section for deriving relative position information of the intra-subject device to the outer surface of the subject; and
   a display device for displaying the position of the intra-subject device relative to the outer surface of the subject based on a result of the detection made by the position detector.

2. The intra-subject position display system according to claim 1, wherein the display device displays an outer surface image of the subject and an image of the intra-subject device disposed in an area corresponding to the relative position of the intra-subject device to the outer surface image.

3. The intra-subject position display system according to claim 1, wherein the position detector comprises:
   a magnetic field sensor for detecting an intensity of a magnetic field generated by a magnetic field generating section included in the intra-subject device;
   a positional relation deriving section for deriving a positional relation between the outer surface of the subject and the magnetic field sensor.

4. The intra-subject position display system according to claim 3, wherein
   the magnetic field sensor is disposed in a fixed positional relation with at least one of the outer surface sensors; and
   the positional relation deriving section derives the positional relation between the outer surface of the subject and the magnetic field sensor based on the position of the at least one outer surface sensor disposed in the fixed positional relation wit the magnetic field sensor.

5. The intra-subject position display system according to claim 3, further comprising a first radio section disposed in a reference position, wherein
   the plurality of outer surface sensors respectively have a second radio section for a transmission of a radio signal to or from the first radio section; and
   the outer surface information deriving section comprises:
   a distance deriving section for deriving a distance between the reference position and the outer surface sensor based on a reception intensity of at least one of the first radio section and the second radio section in the transmission of the radio signal between the first radio section and the second radio section;

an outer surface sensor position deriving section for deriving a position of the outer surface sensor based on the distance derived by the distance deriving section; and an outer surface information deriving section for deriving outer surface information of the subject based on the position derived by the outer surface sensor position deriving section.

6. The intra-subject position display system according to claim 5, wherein each of the second radio sections transmit radio signals having different frequencies from one another; and the outer surface information deriving section further comprises a spectrum analysis section for identifying a transmission source of a received radio signal by analyzing a frequency of the radio signal received by the first radio section.

7. The intra-subject position display system according to claim 5, wherein each of the second radio sections include respective RFID tags storing different identification information from one another; and the outer surface information deriving section further comprises a transmission identifying section for identifying a transmission source of the received radio signal based on the identification information included in the radio signal received by the first radio section.

8. The intra-subject position display system according to claim 5, wherein the outer surface information deriving section further comprises a position information database storing correspondence information between respective distances between the plurality of outer surface sensors and the reference position and the positions of the outer surface sensors; and the outer surface sensor position deriving section derives a position corresponding to the distance derived by the distance deriving section from the information stored in the position information database.

9. The intra-subject position display system according to claim 5, wherein the first radio section comprises a plurality of first radio sections; and the outer surface sensor position deriving section derives distances between a plurality of reference positions corresponding to the respective plurality of first radio sections and the outer surface sensors and derives the positions of the outer surface sensors based on the derived distances.

10. The intra-subject position display system according to claim 5, wherein the outer surface sensor position deriving section further comprises:

an oriented direction adjusting section for adjusting an oriented direction in which the radio signal is transmitted using the first radio section; and an oriented direction determining section for determining a direction causing a highest reception intensity in the transmission of the radio signal to or from the second radio section; and the outer surface sensor position deriving section derives positions of the outer surface sensors based on the distances derived by the distance deriving section and the oriented direction determined by the oriented direction determining section.

11. The intra-subject position display system according to claim 1, wherein the intra-subject device further comprises:

an intra-subject information acquiring section for acquiring intra-subject information; and a radio transmitting section for wirelessly transmitting the intra-subject information acquired by the intra-subject information acquiring section, the intra-subject position display system fhrther comprises a radio receiving section for receiving the radio signal including the intra-subject information transmitted from the radio transmitting section; and the display device further displays a content of the radio signal received by the radio receiving section.

12. The intra-subject position display system according to claim 11, wherein, the intra-subject information acquiring section comprises:

a lighting section for irradiating an inside of the subject; and an imaging unit for acquiring images of the inside of the subject irradiated by the lighting section;

wherein the radio transmitting section transmits a radio signal including image information acquired by taking the images using the imaging unit.

* * * * *

UNITED STATES PATENT AND TRADEMARK OFFICE
CERTIFICATE OF CORRECTION

| | |
|---|---|
| PATENT NO. | : 7,603,160 B2 |
| APPLICATION NO. | : 11/101264 |
| DATED | : October 13, 2009 |
| INVENTOR(S) | : Suzuki et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 819 days.

Signed and Sealed this

Fifth Day of October, 2010

David J. Kappos
*Director of the United States Patent and Trademark Office*